(12) United States Patent
Park et al.

(10) Patent No.: US 10,172,899 B2
(45) Date of Patent: Jan. 8, 2019

(54) **COMPOSITION FOR PREVENTING, TREATING AND IMPROVING OF VOIDING DYSFUNCTION COMPRISING EXTRACT FROM *PIPER LONGUM* L**

(71) Applicant: DONG WHA PHARM. CO., LTD., Seoul (KR)

(72) Inventors: Da-Ae Park, Bucheon-Si (KR); Yoon-Young Chang, Yongin-si (KR); Kwang-Hyun Kim, Yongin-si (KR); Sang-Ho Lee, Yongin-si (KR); Chan-Seok Jeon, Hwaseong-si (KR); Hyun-Yong Lee, Yongin-si (KR)

(73) Assignee: DONG WHA PHARM. CO., LTD., Seoul (KR)

( * ) Notice: Subject to any disclaimer, the term of this patent is extended or adjusted under 35 U.S.C. 154(b) by 0 days.

(21) Appl. No.: 15/795,466

(22) Filed: Oct. 27, 2017

(65) Prior Publication Data

US 2018/0055902 A1    Mar. 1, 2018

Related U.S. Application Data

(63) Continuation-in-part of application No. 15/127,854, filed as application No. PCT/KR2015/002778 on Mar. 20, 2015, now abandoned.

(30) Foreign Application Priority Data

Mar. 21, 2014   (KR) ................ 10-2014-0033513

(51) Int. Cl.
| | |
|---|---|
| *A61K 36/67* | (2006.01) |
| *A23L 33/105* | (2016.01) |
| *A23L 2/52* | (2006.01) |
| *A61K 9/00* | (2006.01) |
| *A61K 9/20* | (2006.01) |
| *A61K 9/48* | (2006.01) |

(52) U.S. Cl.
CPC ............ *A61K 36/67* (2013.01); *A23L 2/52* (2013.01); *A23L 33/105* (2016.08); *A61K 9/0019* (2013.01); *A61K 9/0056* (2013.01); *A61K 9/0095* (2013.01); *A61K 9/20* (2013.01); *A61K 9/48* (2013.01); *A23V 2002/00* (2013.01); *A61K 2236/17* (2013.01); *A61K 2236/331* (2013.01); *A61K 2236/333* (2013.01); *A61K 2236/35* (2013.01); *A61K 2236/53* (2013.01); *A61K 2236/55* (2013.01)

(58) Field of Classification Search
CPC .................................................. A61K 36/67
See application file for complete search history.

(56) References Cited

U.S. PATENT DOCUMENTS 7,014,872 B2 * 3/2006 Pushpangadan ....... A61K 36/00
                                                              424/725

OTHER PUBLICATIONS

Supplementary European Search Report, dated Oct. 18, 2017, corresponding to EP Application No. 15764235.6.
Japanese Office Action, dated Aug. 29, 2017, corresponding to JP Application No. 2016-558351.
Anonymous: "Piper Longum, Long Pepper, Pippal Herb, Benefits, Information", Jun. 2, 2013 (Jun. 2, 2013), XP055410942, Retrieved from the Internet: URL:https://web.archive.org/web/20130602020734/http://www.ayushveda.com/herbs/piper-longum.htm, (retrieved on Sep. 28, 2017).
C. J. Fowler et al: Voiding and the Sacral Reflex Arc: Lessons from Capsaicin Instillation, Scandinavian Journal of Urology and Nephrology, vol. 36, No. 4, Jan. 9, 2002 (Jan. 9, 2002), pp. 46-50, XP055411224.
Rao Venkateswara Gottumukkala et al: "Alkamides and their biological activity from Piper longum Linn", Journal of Pharmacy Research, vol. 5, No. 1, Jan. 1, 2012 (Jan. 1, 2012), pp. 165-168, XP055411333.
Fergal N. McNamara et al: "Effects of piperine, the pungent component of black pepper, at the human vanilloid receptor (TRPV1)", British Journal of Pharmacology, vol. 144, No. 6, Mar. 1, 2005 (Mar. 1, 2005), pp. 181-790, XP055411292.
Chauhan Khushbu et al: "Phytochemical and Therapeutic Potential of Piper Longum Linn A Review", International Journal of Research in Ayurveda and Pharmacy, Feb. 1, 2011 (Feb. 1, 2011), pp. 157-161, XP055411262.
Manish A. Patel et al, "Inhibition of Calcium Oxalate Crystallization by the Fruit Extracts of Piper longum L.", Pharmacologyonline, 2, (2011), vol. 2, pp. 1169-1177.
Maitreyi Saveri et al, "Chemistry and Pharmacology of Piper Longum L", Int. J. Pharm. Sci. Rev. Res., Nov.-Dec. 2010, vol. 5, Issue 1, pp. 67-76.
Gevaert Thomas et al., "TRPV1 Is Involved in Stretch-Evoked Contractile Changes in the Rat Autonomous Bladder Model: A Study with Piperine, a New TRPV1 Agonist", Neurourol. Urodyn., 2007, vol. 26, pp. 440-450.
Teruo Kawada et al., "Some Pungents Principles of Spices Cause the Adrenal Medulla to Secrete Catecholamine in Anesthesized Rats", Proc. Soc. Exp. Biol. Med., 1988, vol. 188, pp. 229-233.
P. D. Hamrapurkar et al, "Quantitative Estimation of Piperine in Piper nigrum and Piper longum Using High Performance Thin Layer Chromatography", J. App. Pharmaceut. Sci., 2011, vol. 1, Iss.3, pp. 117-120.

(Continued)

*Primary Examiner* — Susan Hoffman
(74) *Attorney, Agent, or Firm* — Ladas & Parry LLP; Malcolm J. MacDonald

(57) ABSTRACT

The present invention relates to a pharmaceutical composition for preventing or treating voiding dysfunction and a health functional food for preventing or improving of voiding dysfunction, comprising extract of *Piper Longum* L. as an active ingredient. The extract of *Piper Longum* L. according to the present invention is not only harmless, but also has outstanding effects of preventing, treating and improving voiding dysfunction by being involved in various mechanisms related to voiding dysfunction simultaneously so that it may increase a micturition interval, decrease a micturition pressure, increase a bladder capacity, inhibit detrusor contraction and induce relaxation of detrusor.

14 Claims, 5 Drawing Sheets

(56) References Cited

OTHER PUBLICATIONS

Seon A. Lee, et al, "Piperine from the Fruits of Piper longum with Inhibitory Effect on Monoamine Oxidase and Antidepressant-Like Activity", Chem. Pharm. Bull., 2005, vol. 53, No. 7, pp. 832-835.
Yasuhiko Igawa et al, Beta3-Adrenoceptor Agonists: Possible Role in the Treatment of Overactive Bladder, Korean J. Urol., 2010, vol. 51, pp. 811-818.

* cited by examiner

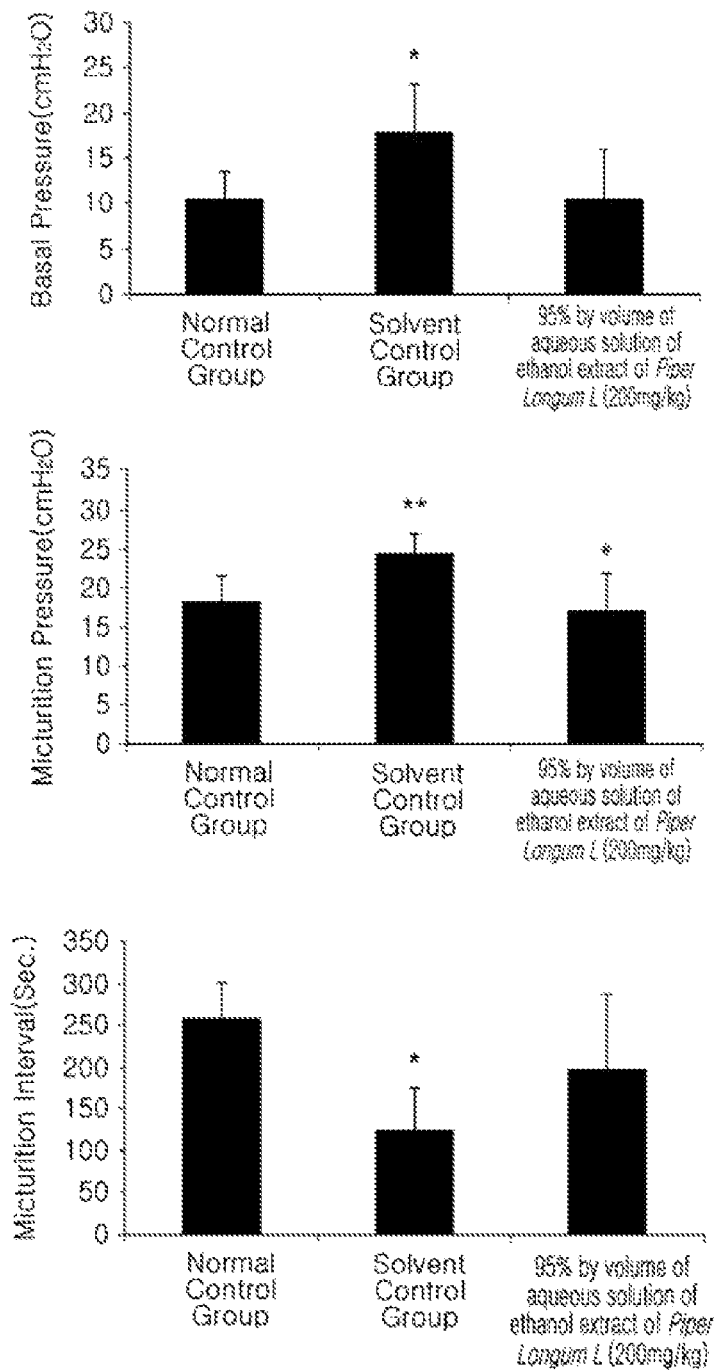
[Fig. 1]

[Fig. 2]
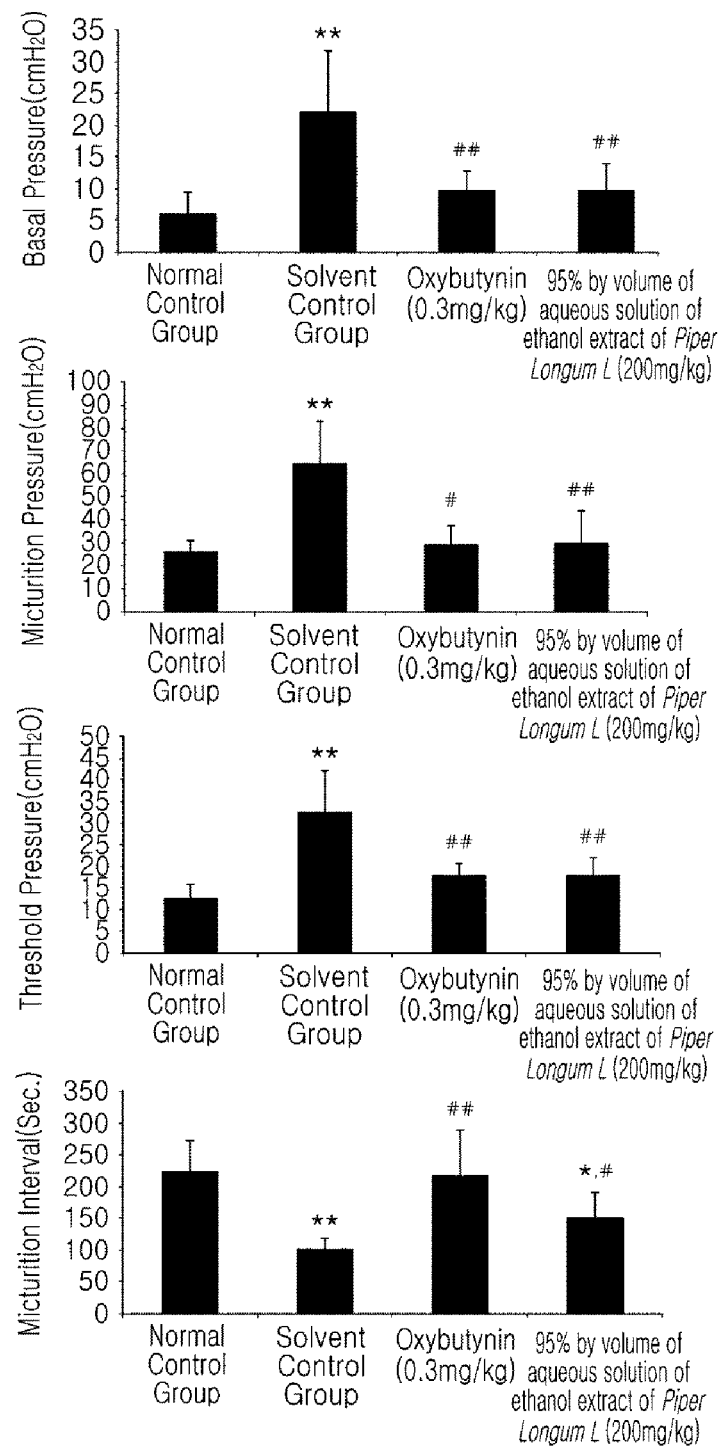

[Fig. 3]
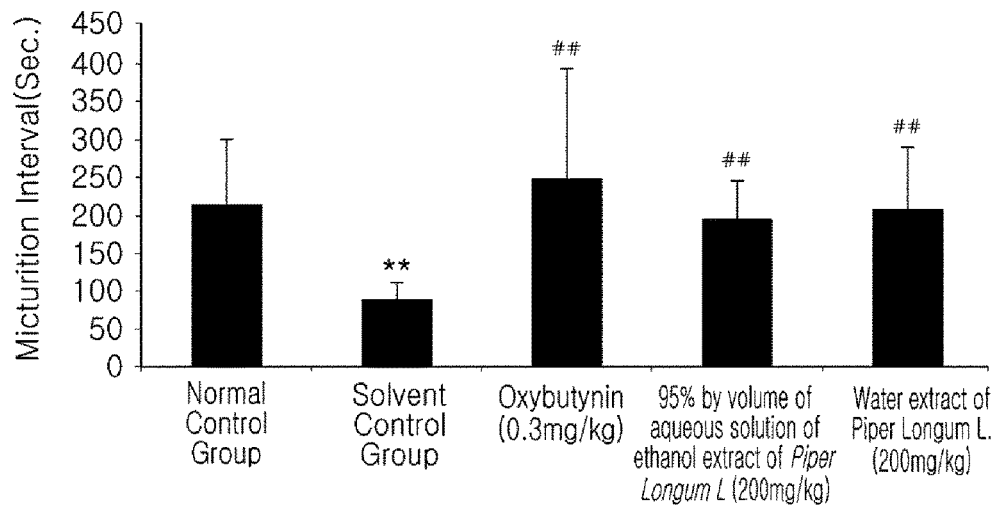
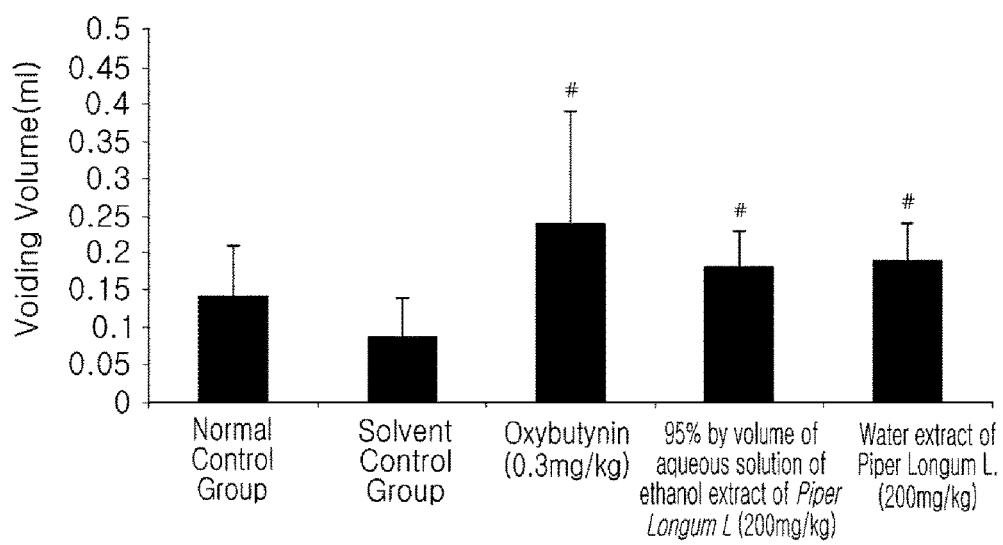

[Fig. 4]
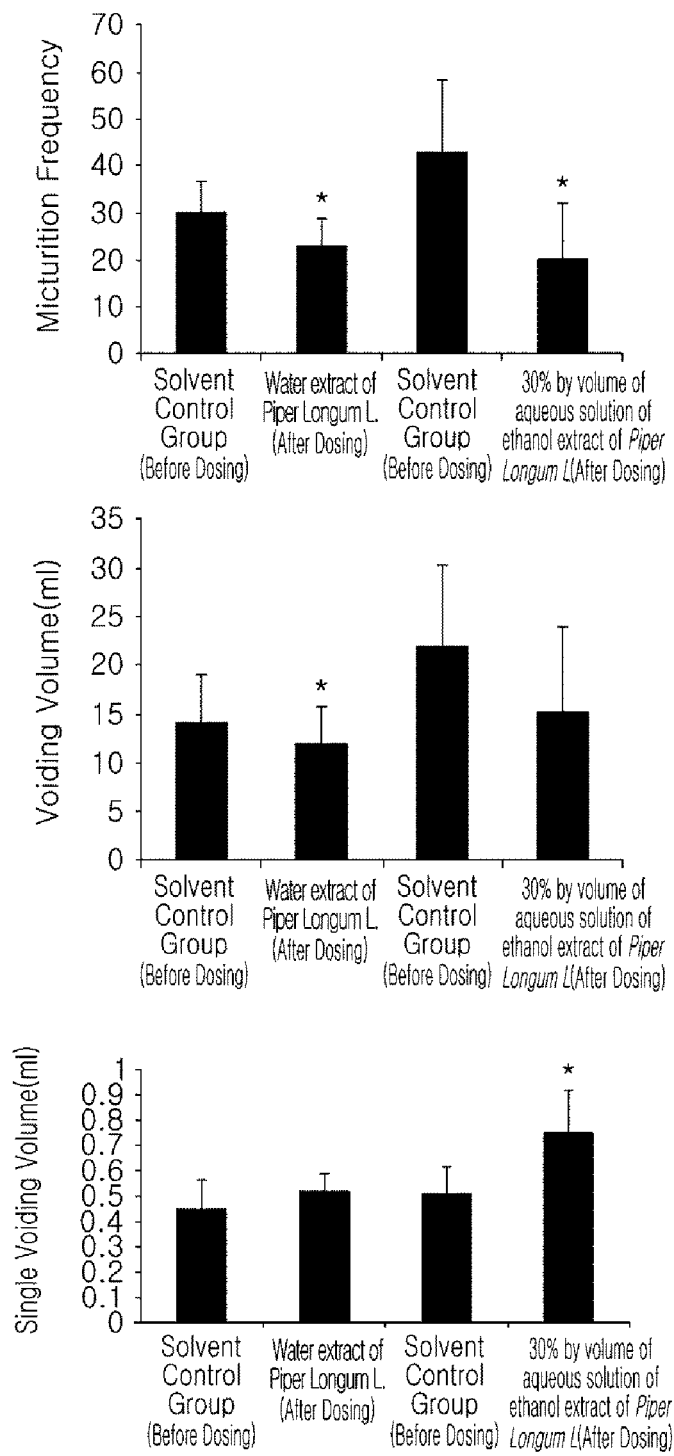

[Fig. 5]
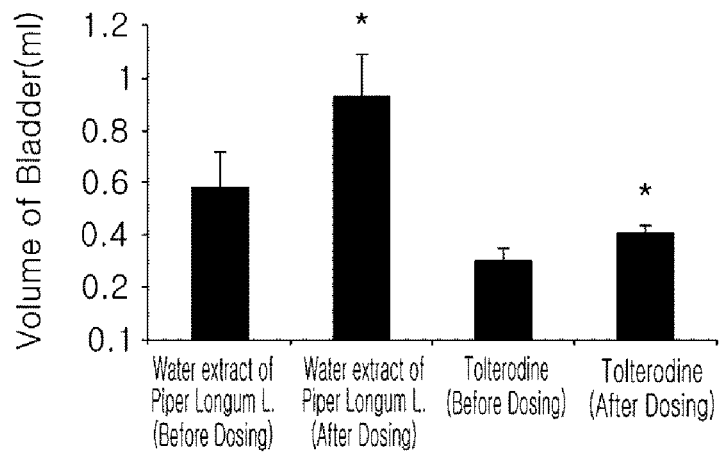
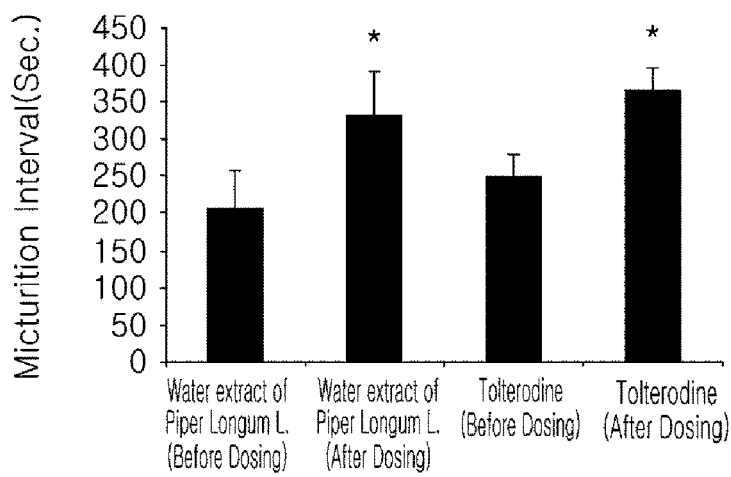
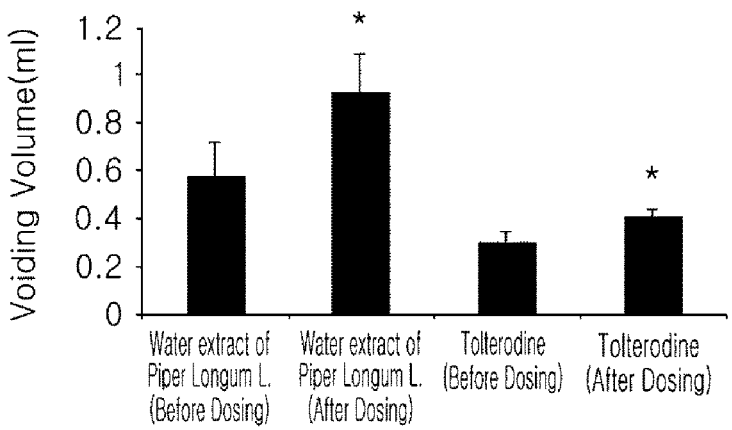

COMPOSITION FOR PREVENTING, TREATING AND IMPROVING OF VOIDING DYSFUNCTION COMPRISING EXTRACT FROM *PIPER LONGUM* L

This application is a continuation-in-part of U.S. application Ser. No. 15/127,854, filed Sep. 21, 2016, now abandoned, which is a 371 of PCT/KR2015/002778 filed Mar. 20, 2015 which claimed foreign priority to Application No. 10-2014-00033513 filed in the Republic of Korea on Mar. 20, 2014.

TECHNICAL FIELD

The present invention relates to a pharmaceutical composition for preventing or treating voiding dysfunction and a health functional food for preventing or improving voiding dysfunction, comprising extract of *Piper longum* L. as an active ingredient.

BACKGROUND ART

Voiding dysfunction is referred to all the urination actions departing from normal voiding patterns. Voiding dysfunction may happen to anyone of men and women, which include neurogenic bladder developed by neurological abnormality, lower urinary tract symptoms and prostatic hyperplasia by non-neurogenic cause, female urinary diseases represented as urinary incontinence (Korean Continence Society, 2003). It was reported that adults have high prevalence in voiding dysfunction, and that while voiding dysfunction increases with their age, men particularly show linear increase. In lower urinary tract symptoms due to voiding dysfunction, all of men and women are believed to have the highest prevalence of storage phase dysfunction symptoms represented as frequent urination and overactive bladder, and it is reported that they develop in turn voiding phase dysfunction, and symptoms after voiding.

Various voiding dysfunction symptoms such as overactive bladder negatively affect health-related quality of individual life in various aspects, since the quality of individual life cannot help being lowered due to restricted intake of beverages, experience of inconvenience to frequently go to toilet, impact on personal relationship and social life, occurrence of health problems or insufficient sleep at night, and the like (Jeung Im KIM, Young Ho KIM, & Hyun Chul AHN, 2002; Yoo Sik LEE, 2001a).

Overactive bladder syndrome (OAB syndrome) is a composite condition group that has recently established a concept of disease, and referred to represent one or more of conditions such as frequent urination (at least 8 times per day), which frequently urinate by frequently contracting bladder in an abnormal way while urine made in kidneys is filled in the bladder, urgency urination, which is hard to hold urine, and thus has to rapidly go to toilet, urgency incontinence, which on urinating does not sufficiently endure urination and leaks urine to soak wears, and nocturia, which has to urinate one or more times during sleep at night, regardless of being urgency incontinence, provided that there is no urinary tract infection and other clear etiology. Conditions of overactive bladder are related to involuntary contraction to result in state of bladder hyperactivity.

As the bladder consists of smooth muscles and voiding function is regulated by nervous system, various voiding dysfunction may be developed by abnormality of the smooth muscles and the nervous system. It is not still clearly known about main causes of diseases, since overactive bladder is generally developed by a neurogenic cause derived from brain diseases or spinal cord injuries, bladder outlet obstruction represented as male prostatic hyperplasia, weakness of pelvis structure of female, local diseases of urethra and bladder, and the like, but there are many cases caused by aging of detrusor myocytes, obscure dysfunction of detrusor, and the like (Tae Hyung KIM, Journal of Chung Ang University College of Medicine 28(3), p 143-149, 2003).

While the overactive bladder syndromes are not one process of aging, event probability increases with age. Urgency incontinence is more common developed in women, although the ratio of men to women is similar. It is variously reported from 12.7% to 30.5% at home, and in accordance with one research in Europe, the overactive bladder is a common disease such that it is developed in men at 16% and in women at 17%, over age 40, and specifically in men at 42% and in women at 31%, over age 75, and these statistics are also similar to developed countries such as USA and Japan (2011, Korean Continence Society, Guidelines on Overactive Bladder). The overactive bladder showed decrease in quality of life by affecting basic physical activity, sex life, and moreover social activity socially and mentally, and as a result of surveying HRQOL (health-related quality-of-life) for patients, it showed to have higher impact on quality of life than diabetes (Liberman J N, Hunt T L, Stewart W F, Wein A, Zhou Z, Herzog A R, et al. Health-related quality of life among adults with symptoms of overactive bladder: results from a U.S. community-based survey. Urology 2001; 57:1044-50).

Although antimuscarinic drugs are now widely used as an initial standard treatment of the overactive bladder, there is still no report for internationally practiced and controlled clinical trials to certainly demonstrate effectiveness, and it is reported that since these drugs have anticholinergic property affected across nervous system, adverse effects such as thirst, constipation, blurred vision and acute urinary retention are occurred at the rate of 1-2 in 10 people. Such adverse effects are reported as one cause to lower drug compliance in case of patients with voiding dysfunction needed regulated water intake, and for this reason, it is consistently required for development of novel alternative drugs for voiding dysfunction such as overactive bladder (J. Korean Continence Soc 2009; 13:7-22).

Urgency incontinence is for involuntary urine leakage to be suddenly developed after a severe condition of urine urgency, in which its causal factor is known as particular scene, sounds, contact with running water, position change, and the like. Urgency urine is also called urine urgency and referred to a condition that a desire intended to urinate suddenly occurs, and means a state that once one feels a sense for urination, he does not endure urination. In this case, it is known that if one does not immediately urinate, pain may be induced, and severely, the bladder may arbitrarily contact to proceed into urgency incontinence leaking urine. Frequent urination was defined as a case of urinating 8 times or more for 24 hours, unlike normal adults urinating 4~6 times per day with a voiding volume at a time of about 300 cc, but the definition of frequent urination was extended by defining it by the International Continence Society in 2002 as a case that a patient himself feels to very frequently urinate. Frequent urination is caused by excess water intake, detrusor hyperactivity, bladder capacity decrease, supersensitivity of bladder, and the like to be one of representative conditions of voiding dysfunction referred to abnormal voiding conditions. Nocturnal urine is referred to urinate after waking up during sleep at night, which is classified as nocturnal polyuria that a night voiding volume is relatively high over the daily voiding volume and nocturia that does not. To be defined as nocturnal urine, it should be necessary accompanied by sleep before and after voiding, and the patient with nocturia frequently wakes up and does not fall asleep easily, so that he is sleepy and tired in the daytime due to disturbed sleep to result in inconvenience in his daily life. Furthermore, an elderly person has a problem to increase risk of fall or fracture. Nocturia is reported to be associated with various factors such as age, life habit, polyuria, nocturnal polyuria, bladder disorder, sleep disorder, and psychological factor. Interstitial cystitis is also called bladder pain syndrome or chronic cystitis. There was no characteristic pathologic manifestation such as bacterial infection, and the exact cause was not still found. Although it is known that this develops, as defects occur in bladder epithelial cells to damage bladder mucosal lining between urine and blood flow, inflammation in bladder or vascular disorders of bladder, bladder mucosal damages and psychosomatic disorders may serve as an inducer. While this occurs in all of men and women, the extent of 90% is revealed to female, mostly, in mid-forties. Abnormal sensory urgency urination and frequent urination are developed as symptoms, with chiefly complaining bladder pain. When urine is filled, the symptoms become worse, while those have less pain on voiding. With urinating 1~2 times or more and an average of 4 times at night, there is less hematuria. With urinating at least 8 times or more and an average of 16 times in the daytime, the normal person has a voiding volume at a time of 250 ml, while the patient suffering from this disease has an average volume of 75 ml. 3 in 4 patients have more severe symptoms due to sex conducts, and menstruation cycles, stress, foods and the like also affect deterioration of symptoms. For treatment, following administration of an antidepressant and anesthesia, an operation such as bladder hydrodistention, cystolysis, bladder enlargement, urinary diversion is implemented or a drug such as an anticholinergic drug or alpha-adrenergic receptor blocker, an antihistaminic drug, a steroid, silver nitrate, heparin is administrated, but the effect of treatment is not high, and thus it is required for novel drugs to treat such voiding dysfunction.

Meanwhile, *Piperis Longi* Fructus native to India as a fruit of *Piperis Longum* L. being a climbing woody plant of Piperaceae is cultivated in China and Indonesia to be imported into Korea, which is used under the oriental medicine name of Pilbal at home.

*Piper Longum* L. contains various components such as essential oils (camphene, piperonal, sabinene, limonene, myrcene), a fatty acid (palmitic acid) and alkaloids (piperidine, piperine, piperannine), has an effect of alleviating pain in hot body as an interior warming medicine warming the spleen and stomach, in the oriental medicine and is referred to be used in dysentery, vomit, abdominal inflation, toothache, analgesia and diarrhea. In India, Ayurveda, *Piper Longum* L. is currently used under the name of PIPPALI, and referred to have been used as a digestive stimulator, a carminative, an expectorant, a bronchodilator, an anthelmintic, a sedative, a circulation stimulator, an aphrodisiac (Traditional Medicine of India, Shinilbooks, December 2011), and as pharmaceutical actions of *Piper Longum* L., antibacterial, anticonvulsant, skin vasodilatation, antioxidation, antimyocardial ischemia, antilipidemic, anticancer and antiobestic actions have been reported. However, it is not still known about an effect of improving voiding dysfunction with *Piper Longum* L.

DISCLOSURE

Technical Problem

While the present inventors have intensively studied natural products being capable of preventing, treating and improving effectively various voiding dysfunction, they have found that extract of *Piper Longum* L. is not only harmless, but also reveals outstanding effects of preventing, treating and improving voiding dysfunction by being involved in various mechanisms related to voiding dysfunction simultaneously, and thus completed the present invention.

Accordingly, the present invention is intended to provide a pharmaceutical composition for preventing or treating voiding dysfunction comprising extract of *Piper Longum* L. as an active ingredient.

Furthermore, the present invention is intended to provide a health functional food for preventing or improving voiding dysfunction comprising extract of *Piper Longum* L. as an active ingredient.

Technical Solution

The present invention provides a pharmaceutical composition for preventing or treating voiding dysfunction comprising extract of *Piper Longum* L. as an active ingredient.

Furthermore, the present invention provides a pharmaceutical composition for preventing or treating voiding dysfunction; wherein the extract of *Piper Longum* L. is extracted from one or more extraction solvents selected from the group consisting of water, alcohol, glycerin, butylene glycol, propylene glycol, methyl acetate, ethyl acetate, acetone, benzene, hexane, diethyl ether, chloroform and dichloromethane. Preferably, the extraction solvent may be one or more extraction solvents selected from the group consisting of water, alcohol, ethyl acetate, n-hexane, chloroform, dichloromethane. More preferably, the extraction solvent may be water, alcohol or hydrous alcohol (aqueous alcohol solution). The alcohol may be methanol, ethanol or isopropanol. Still more preferably, the extraction solvent may be water or hydrous ethanol (aqueous solution of ethanol).

Furthermore, the present invention provides a pharmaceutical composition for preventing or treating voiding dysfunction, wherein the alcohol is anhydrous or hydrous lower alcohol with 1 to 4 carbon atoms. Preferably, the alcohol may be hydrous methanol (aqueous methanol solution) or hydrous ethanol. More preferably, the alcohol may be hydrous ethanol (aqueous solution of ethanol).

Furthermore, the present invention provides a pharmaceutical composition for preventing or treating voiding dysfunction, wherein the anhydrous or hydrous lower alcohol is 30 to 100% by volume of methanol or ethanol. Preferably, the hydrous lower alcohol may be 30 to 100% by volume (volume/volume; vol/vol) of aqueous solution of ethanol. More preferably, the hydrous lower alcohol may be 30 to 95% by volume of aqueous solution of ethanol. Still more preferably, the hydrous lower alcohol may be 95% by volume of aqueous solution of ethanol.

Furthermore, the present invention provides a pharmaceutical composition for preventing or treating voiding dysfunction, wherein the extract of *Piper Longum* L. is a polar solvent-soluble extract or non-polar solvent-soluble extract. The polar solvent-soluble extract may be an extract soluble in a solvent selected from water, methanol, butanol or mixed solvents thereof, and preferably, an extract soluble in saturated n-butanol, and the non-polar solvent-soluble extract may be an extract soluble in dichloromethane or ethyl acetate.

Furthermore, the present invention provides a pharmaceutical composition for preventing or treating voiding dysfunction, wherein the extract of *Piper Longum* L. increases a micturition interval.

Furthermore, the present invention provides a pharmaceutical composition for preventing or treating voiding dysfunction, wherein the extract of *Piper Longum* L. decreases a micturition pressure and increases a bladder capacity.

Furthermore, the present invention provides a pharmaceutical composition for preventing or treating voiding dysfunction, wherein the extract of *Piper Longum* L. induces inhibition of detrusor contraction and relaxation of detrusor.

Furthermore, the present invention provides a pharmaceutical composition for preventing or treating voiding dysfunction, wherein the extract of *Piper Longum* L. inhibits a muscarinic $M_3$ receptor or a muscarinic $M_2$ receptor.

Furthermore, the present invention provides a pharmaceutical composition for preventing or treating voiding dysfunction, wherein the extract of *Piper Longum* L. is an agonist of a $\beta_3$-adrenegic receptor.

Furthermore, the present invention provides a pharmaceutical composition for preventing or treating voiding dysfunction, wherein the voiding dysfunction is one or more selected from the group consisting of overactive bladder syndrome, urgency incontinence, urgency urine, frequent urination, nocturia and interstitial cystitis.

Furthermore, the present invention provides a health functional food for preventing or improving voiding dysfunction comprising the extract of *Piper Longum* L. as an active ingredient.

Furthermore, the present invention provides a health functional food for preventing or improving voiding dysfunction, wherein the voiding dysfunction is one or more selected from the group consisting of overactive bladder syndrome, urgency incontinence, urgency urine, frequent urination, nocturia and interstitial cystitis.

Furthermore, the present invention provides a pharmaceutical composition for preventing or treating voiding dysfunction, wherein the extract of *Piper Longum* L. is a polar solvent-soluble extract or non-polar solvent-soluble extract.

Furthermore, the present invention is intended to provide a pharmaceutical composition comprising as an active ingredient the extract of *Piper Longum* L. for use in preventing or treating voiding dysfunction.

Furthermore, the present invention is intended to provide a composition comprising as an active ingredient the extract of *Piper Longum* L. for use in preventing or improving voiding dysfunction.

Furthermore, the present invention is intended to provide a use of the extract of *Piper Longum* L. for preparing a pharmaceutical formulation for preventing or treating voiding dysfunction.

Furthermore, the present invention is intended to provide a method of preventing or treating voiding dysfunction by administrating to a subject including a mammal a pharmaceutical composition for preventing or treating voiding dysfunction comprising extract of *Piper Longum* L. as an active ingredient.

Advantageous Effects

The extract of *Piper Longum* L. according to the present invention is not only harmless, but also has outstanding effects of preventing, treating and improving voiding dysfunction by being involved in various mechanisms related to voiding dysfunction simultaneously so that it may increase a micturition interval, decrease a micturition pressure, increase a bladder capacity, inhibit detrusor contraction and induce relaxation of detrusor.

DESCRIPTION OF DRAWINGS

FIG. 1 shows a result of comparing changes in a basal pressure (BP), a micturition pressure (MP) and a micturition interval (MI) after administrating 95% by volume of aqueous solution of ethanol extract (200 mg/kg) of the *Piper Longum* L. with normal control group and solvent control group.

FIG. 2 shows a result of comparing changes in a basal pressure (BP), a micturition pressure (MP), a threshold pressure (TP) and a micturition interval (MI) after administrating 95% by volume of aqueous solution of ethanol extract (200 mg/kg) of the *Piper Longum* L. with normal control group, solvent control group, and positive control group (oxybutynin).

FIG. 3 shows a result of comparing changes in a micturition interval (MI) and a voiding volume (VV) after administrating water extract (200 mg/kg) and 95% by volume of aqueous ethanol solution extract (200 mg/kg) of the *Piper Longum* L.

FIG. 4 shows a result of comparing changes in a micturition frequency, total voided volume and a volume per void after administrating water extract (300 mg/kg) and 30% by volume of aqueous solution of ethanol extract (300 mg/kg) of the *Piper Longum* L.

FIG. 5 shows a result of comparing changes in a bladder capacity (BC), a voiding volume (VV) and a micturition interval (MI) before and after administrating water extract (300 mg/kg) of the *Piper Longum* L. with a positive control group (tolterodine).

BEST MODE

The present invention provides a pharmaceutical composition for preventing or treating voiding dysfunction comprising the extract of *Piper Longum* L. as an active ingredient.

The extract of *Piper Longum* L. according to the present invention is not only harmless, but also involved in various mechanisms related to voiding dysfunction simultaneously so that it may increase a micturition interval, decrease a micturition pressure, increase a bladder capacity, inhibit detrusor contraction and induce relaxation of detrusor. It is supposed that the effects of preventing, treating and improving voiding dysfunction with the extract of *Piper Longum* L. according to the present invention result from the fact that extract of *Piper Longum* L. inhibits a muscarinic $M_3$ receptor or a muscarinic $M_2$ receptor or activates a $\beta_3$-adrenegic receptor, which is involved in contraction and relaxation of bladder in enteric nervous system of spinal cord and upper spinal cord pathway as well as in bladder. However, the scope of the present invention is not restricted by the above mechanism.

The "*Piper Longum* L." according to the present invention may be utilized without limitation, from those which are cultivated, collected or marketed, and comprise stems, leaves, roots and fruits thereof as long as they reveal effects of preventing, treating or improving voiding dysfunction, and preferably, fruits of the *Piper Longum* L.

The extract of *Piper Longum* L. according to the present invention may be one that is extracted from a usual extraction solvent, which includes, but not limited to, for example, water; anhydrous or hydrous alcohol; polyalcohol such as glycerin, butylene glycol, and propylene glycol; hydrocarbon-based solvents such as methyl acetate, ethyl acetate, acetone, benzene, hexane, diethyl ether, and dichloromethane; or mixtures thereof. In addition, the extract of *Piper Longum* L. according to the present invention may be one that is extracted from one or more extraction solvents, preferably, selected from the group consisting of water, alcohol, glycerin, butylene glycol, propylene glycol, methyl acetate, ethyl acetate, acetone, benzene, hexane, diethyl ether, chloroform and dichloromethane. Preferably, the extraction solvent may be one or more extraction solvents selected from the group consisting of water, alcohol, ethyl acetate, n-hexane, chloroform, dichloromethane. More preferably, the extraction solvent may be water, alcohol or hydrous alcohol. The alcohol may be methanol, ethanol or isopropanol. Still more preferably, the extraction solvent may be water or hydrous ethanol.

In addition, preferably, the extract of *Piper Longum* L. according to the present invention may be one that is extracted with anhydrous or hydrous lower alcohol with 1 to 4 carbon atoms as an extraction solvent, wherein the anhydrous or hydrous lower alcohol with 1 to 4 carbon atoms may be 10 to 100% by volume, preferably 30 to 100% by volume, still preferably 70 to 100% by volume of methanol or ethanol. Preferably, the extraction solvent may be water or 30 to 95% by volume of ethanol. Hereinafter, '% alcohol' as described herein is used in the same meaning as '% by volume alcohol.'

It is preferred that the extract of *Piper Longum* L. is prepared by a process for preparing comprising the following steps, but it is not limited thereto.

(1) Chopping *Piper Longum* L. after drying;
(2) Adding an extraction solvent to the chopped *Piper Longum* L. to extract an extract;
(3) Filtering the extract after cooling; and
(4) Concentrating the filtered extract.

The *Piper Longum* L. used in Step (1) may be utilized, without limitation, from those which are cultivated, collected or marketed, and the drying in Step (1) is preferably by air drying in the shade.

The extraction in Step (2) may be utilized from an extraction method, such as, but not limited to, stirring extraction, reflux cooling extraction, cryoprecipitation extraction, ultrasonic extraction, and supercritical extraction. An extraction temperature is preferably 50 to 120° C., and more preferably 80 to 100° C. Also, an extraction time is preferably 1 to 20 hours, and more preferably 2 to 5 hours. In addition, a frequency of extraction may be 1 to 5 times, more preferably 2 or 3 times. Furthermore, the extraction in Step (2) may be made by adding the extraction solvent to the *Piper Longum* L. by a factor of 1 to 10 based on the volume of the *Piper Longum* L.

Although the filtering in Step (3) may be performed with 100~500 mesh, it is preferred to utilize 300 mesh.

The concentration in Step (4) may be made at 10 to 100° C., preferably 50 to 80° C., and it is preferred to utilize vacuum concentrator or vacuum rotary evaporator.

Furthermore, in addition to the above process, it may comprise further a step of drying as Step (5), wherein the drying may be made using reduced-pressure drying, vacuum drying, boil drying, spray drying or lyophilizing method.

Furthermore, the extract of *Piper Longum* L. according to the present invention may comprise an extracted fraction of the extract of *Piper Longum* L. The extracted fraction of the extract of *Piper Longum* L. may be obtained from the extract of *Piper Longum* L. obtained by using anhydrous or hydrous lower alcohol with 1 to 4 carbon atoms as an extraction solvent via a method to generally obtain fractions in the art such as concentration gradient column chromatography using a mixed solvent of anhydrous or hydrous alcohol with 1 to 4 carbon atoms or acetonitrile and water as a mobile phase.

Furthermore, the present invention provides a pharmaceutical composition for preventing or treating voiding dysfunction, wherein the extract of *Piper Longum* L. is a polar solvent-soluble extract or non-polar solvent-soluble extract. The polar solvent-soluble extract may be an extract soluble in a solvent selected from water, methanol, butanol or mixed solvents thereof, and preferably, an extract soluble in saturated n-butanol, and the non-polar solvent-soluble extract may be an extract soluble in dichloromethane or ethyl acetate. Preferably, it may be one which is fractional extracted by a process for preparing which comprises adding water and dichloromethane to the aqueous solution of ethanol extract of the *Piper Longum* L. to prepare dichloromethane-soluble extract and dichloromethane-non-soluble extract (aqueous layer), adding water and ethyl acetate to the dichloromethane-non-soluble extract to prepare ethyl acetate-soluble extract and ethyl acetate-non-soluble extract (aqueous layer), and adding water and saturated n-butanol to the ethyl acetate-non-soluble extract to prepare saturated n-butanol-soluble extract and saturated n-butanol-non-soluble extract (aqueous layer). The aqueous solution of ethanol may be 30 to 95% by volume of aqueous solution of ethanol, and more preferably, the hydrous lower alcohol may be 95% by volume of aqueous solution of ethanol.

The extract of *Piper Longum* L. according to the present invention may be involved in cAMP signaling pathway of $\beta_3$-adrenegic receptor as well as an antimuscarinic mechanism conventionally being a target of therapeutic agents for voiding dysfunction to target composite mechanisms involved in voiding dysfunction, and thus reveal effects of improving voiding dysfunction.

Accordingly, the extract of *Piper Longum* L. according to the present invention may decrease micturition pressure, and increase bladder capacity. In addition, extract of *Piper Longum* L. according to the present invention may induce inhibition of detrusor contraction and relaxation of detrusor.

Furthermore, the extract of *Piper Longum* L. according to the present invention may inhibit a muscarinic $M_3$ receptor or a muscarinic $M_2$ receptor, and be agonists of a $\beta_3$-adrenegic receptor.

$M_3/M_2$ receptors are receptors affecting parasympathetic nerves, which are distributed in eye, urinary organs, gastrointestinal tracts, cardiovascular system, and their related diseases or symptoms include chronic obstructive pulmonary disease, chronic bronchitis, asthma, adult/acute respiratory distress syndrome, chronic respiratory obstruction, bronchial hyperactivity, pulmonary fibrosis, emphysema or allergic rhinitis, irritable bowel syndrome, convulsive colitis, gastroduodenal ulcer, gastrointestinal convulsion or hyperanakinesia, diverticulitis, pain accompanying convulsion of gastrointestinal soft muscle; voiding dysfunction including neurogenic sychnuria, neurogenic bladder, enuresis, psychosomatic bladder, incontinence related to bladder convulsion or chronic cystitis, overactive bladder syndrome, urgency or sychnuria.

$\beta_3$-adrenegic receptors are distributed in bladder corpus as well as white adipocytes and brown adipocytes, and their related diseases or symptoms include overweight, obesity, glucose tolerance disorder, diabetes mellitus type 1, diabetes mellitus type 2, urgency urine, enuresis and voiding dysfunction including incontinence, neurogenic bladder, overactive bladder syndrome, urgency or sychnuria.

Therefore, "voiding dysfunction" according to the present invention may include various dysfunctions departing from normal voiding patterns representing as regards micturition, and be dysfunctions representing due to detrusor underactivity such as detrusor abnormal contraction or relaxation, detrusor instability, sensory urgency urine, and the like. In particular, the voiding dysfunction may include, preferably, storage symptoms including sychnuria, nocturia, urgency urine, incontinence, enuresis; voiding symptoms including weak stream, splitting, intermittency, urinary hesitancy, abdominal straining voiding, terminal dribbling; symptoms after voiding including residual urine sense, postmicturition dribble or interstitial cystitis, and the like, and more preferably, be one or more selected from the group consisting of overactive bladder syndromes, urgency incontinence, urgency urine, sychnuria, nocturia and interstitial cystitis.

Furthermore, to prevent, treat or improve voiding dysfunction, the pharmaceutical composition according to the present invention may be used alone or in combination with operation, hormone treatment, drug treatment and methods using biologic response modifiers.

The pharmaceutical composition according to the present invention may be formulated by adding a pharmaceutically acceptable carrier thereto, and details for formulation may be referenced in Remington's Pharmaceutical Science (recent edition), Mack Publishing Company, Easton Pa. The pharmaceutically acceptable carrier means one that ordinary skilled person in the pharmaceutical invention field usually use on preparing pharmaceutical compositions. For example, it includes lactose, dextrose, sucrose, sorbitol, mannitol, xylitol, erythritol, maltitol, starch, gum acasia, alginate, gelatin, calcium phosphate, calcium silicate, cellulose, methyl cellulose, microcrystalline cellulose, polyvinyl pyrrolidone, water, methyl hydroxybenzoate, propylhydroxybenzoate, talc, magnesium stearate, and mineral oil, and the like. In addition, the pharmaceutically acceptable carrier includes diluents or excipients such as fillers, extenders, binders, wetting agents, disintegrating agents, and surfactants.

A solid formulation for oral administration include tablet, pill, powder, granule and capsule, and such solid formulation is prepared by mixing the pharmaceutical composition of the present invention with at least one of excipient such as starch, calcium carbonate, sucrose, lactose, sucrose, lactose, gelatin, and the like. Also, in addition to the simple excipient, lubricant such as magnesium stearate, talc may be used.

A liquid formulation for oral administration, which corresponds to suspensions, internal drugs, emulsions and syrups, may include various excipients, for example, wetting agents, sweeting agents, aromatic agents and preservatives as well as water and liquid paraffin as simple diluents being common used.

As examples for percutaneous administration, carriers and/or excipients may be mentioned, which are suitable to produce dusting powders, emulsions, suspensions, oils, sprays, ointments, greasy ointments, cream pastes, gels, foams, or solutions, and suitable to transdermal therapeutics system (TTS). Local pharmaceutical formulations according to the present invention may be semi-solid dosage forms, and specifically ointments (solution ointments, suspension ointments), creams, gels, or pastes. The following is mainly used in the oily phase: fatty alcohol, such as lauryl alcohol, cetyl alcohol, stearyl alcohol, fatty acid, such as palmitic acid or steraric acid, liquid or solid paraffin or ozokerite, liquid or solid wax, such as isopropyl myristate, natural fat or partial synthetic fat, such as coconut fatty acid triglyceride, hardened oil, such as hydrogenated peanut or castor oil, or fatty acid partial ester of glycerol, such as glycerol monostearate or glycerol distearate. Suitable emulsifiers include surfactants, such as nonionic surfactants, for example, fatty acid ester of polyalcohol or ethylene oxide adducts thereof, e. g. polyglycerol fatty acid ester or polyoxyethylene sorbitan fatty acid ester, sorbitan fatty acid ester, for example, sorbitan oleate and/or sorbitan isostearate, isostearate, sterol, or polyoxyethylene fatty alcohol ether or fatty acid ester; anionic surfactants, for example, alkali metal salts of fatty alcoholsulfate, e. g. sodium lauryl sulfate, sodium cetyl sulfate or sodium stearyl sulfate, which are generally used in presence of the above fatty alcohol, for example cetyl alcohol or stearyl alcohol. Among these, it is possible to add a formulation inhibiting dryness of cream, such as polyalcohol, for example, glycerol, sorbitol, propylene glycol and/or polyethylene glycol to the aqueous phase or add a preservative, a fragrance, and the like to the aqueous phase.

However, the present invention is not restricted by the pharmaceutically acceptable carriers as listed above, which are only exemplary.

Although an application amount of the extract of *Piper Longum* L. contained in the pharmaceutical composition vary depending on state and weight of a patient, severity of illness, drug forms, route of administration and period, it can be suitably selected, if necessary. The term "administration" herein means to introduce a composition for preventing or treating voiding dysfunction according to the present invention into a patient by any suitably method, and the route of administrating the composition for preventing or treating voiding dysfunction according to the present invention may be any general route as long as it can reach to target tissues. For example, the extract of *Piper Longum* L. may be administrated in a dosage of 1 to 2400 mg/day, preferably 10 to 1000 mg/day, based on an adult weighing 60 kg, with being applied once or several times a day. Also, the pharmaceutical composition may comprise the extract of *Piper Longum* L. in an amount of 0.0001 to 50% by weight relative to the total weight of the composition. The pharmaceutical composition may be applied on a mammal such as human by various routes, for example, percutaneous, oral, intravenous, intramuscular, or subcutaneous injection.

Furthermore, the present invention provides a health functional food for preventing or improving voiding dysfunction comprising the extract of *Piper Longum* L. as an active ingredient.

The health functional food according to the present invention includes foods defined in Functional Health Foods Act legislated on Aug. 26, 2002 in Korea. Specifically, the "health functional food" includes a food which is prepared or processed in a form of tablet, capsule, powder, granule, liquid, pill, and the like by using raw materials or components having useful functions in human body.

The voiding dysfunction may include various dysfunctions departing from normal voiding patterns representing as regards micturition, and be dysfunctions representing due to detrusor underactivity such as detrusor abnormal contraction or relaxation, detrusor instability, sensory urgency urine, and the like, and preferably, be one or more selected from the group consisting of overactive bladder syndromes, urgency incontinence, urgency urine, sychnuria, nocturia and interstitial cystitis.

The health functional food may contain various nutrients, vitamins, minerals (electrolytes), flavoring agents such as synthetic flavoring agents and natural flavoring agents, colorants and enhancers (cheese, chocolate, and the like), pectic acid and salts thereof, alginic acid and salts thereof, organic acids, protective colloid thickeners, pH regulators, stabilizers, preservatives, glycerin, alcohol, carbonating agents used in carbonated drinks, and the like, and moreover natural fruit juices and pulps for preparing fruit juice drinks and vegetable drinks. Such components may be used independently or in combination therewith.

The health functional food may be any one form of meat, sausage, bread, chocolate, candies, snacks, confectionaries, pizza, ramen, gums, ice creams, soups, drinks, tea, functional water, health drinks, alcoholic beverages and vitamin composites.

The health functional food may further comprise food additives, for which compatibility as "food additives" is decided by standards and criteria on corresponding items in accordance with general rules and general test methods of Food Additives Codex approved by Ministry of Food and Drug Safety in Korea, unless there are other rules.

Items listed in the "Food Additives Codex" may include, for example, chemical synthetics such as ketones, glycin, potassium citrate, nicotinic acid and cinnamic acid, natural additives such as persimmon color, licorice extract, crystalline cellulose, kaoliang color and guar gum, mixed formulations such as L-sodium glutamate formulations, alkali agents for noodles, preservative formulations and tar color formulations.

The extract of *Piper Longum* L. according to the present invention added to food including beverage during procedures to prepare the health functional food according to the present invention may suitably decrease or increase the content, if needed, and preferably, it is preferred to add it in the range of 1 to 15% by weight relative to 100% by weight of the total food.

The numerical values described in the specification should be interpreted to include equivalent ranges, unless otherwise indicated.

Next, to help understanding the present invention, preferred preparation examples, examples and formulation examples are described. However, the following preparation examples, examples and formulation examples are only provided to easily understand the present invention, which is not restricted by the preparation examples, examples and formulation examples. In the following preparation examples 1 to 5, for preparation of the extract of *Piper Longum* L., its fruits purchased from BooYoung Oriental Medicine (147 Wangsan-ro, Dongdaemun-ku, Seoul) in GyeungDong Market were used.

Preparation Example 1: Preparation of the Extract of *Piper Longum* L.

Preparation Example 1-1: Preparation of the Water Extract of *Piper Longum* L.

1 L of water was added to 100 g of the fruits of *Piper Longum* L. dried in shade to be extracted in a constant temperature water bath (HYNDAE Science, B-90) at 95° C. for 3.5 hours under reflux. The resulting extract was filtered with a filter paper under reduced pressure, and then the resulting filtrate was reduced pressure concentrated with a vacuum rotary evaporator (EYELA, N-1100) under a condition of 50-60° C. to yield 9.6 g±0.1 g of soft extract of the extract of *Piper Longum* L. (the water extract of *Piper Longum* L.), which was used as a sample for toxicity identification experiment below.

Preparation Example 1-2: Preparation of 30% by Volume of Aqueous Solution of Ethanol Extract of *Piper Longum* L.

To prepare 30% by volume of aqueous solution of ethanol extract, 1 L of 30% by volume of aqueous solution of ethanol was added to 120 g of the fruits of *Piper Longum* L. dried in shade to be extracted in a constant temperature water bath (HYNDAE Science, B-90) at 85-95° C. for 3.5 hours under reflux. The resulting extract was filtered with a filter paper under reduced pressure, and then the resulting filtrate was evaporative concentrated with a vacuum rotary evaporator (EYELA, N-1100) under a condition of 50-60° C. and dried with a vacuum dryer (JE10 Tech, OV-12) for at least 12 hours to yield 10.86 g of 30% by volume of aqueous solution of ethanol extract of the *Piper Longum* L., which was used as a sample for toxicity identification experiment below.

Example 1: Toxicity Identification of the Extract of *Piper Longum* L.

1.1 Acute Toxicity Experiment

The acute toxicity study was performed using 6 week-old specific pathogen-free (SPF) SD male and female rats (ORIENT, Korea). The animals were divided into 5 rats per group. Water extract of the *Piper Longum* L. prepared in Preparation Example 1.1 was orally administered once at a single dose of 2 g/kg. After administration of experimental material, mortality, clinical symptom and change of body weight were observed and, gross finding of organs in abdominal and thoracic cavity was performed after necropsy. As a result, there were no dead animals and abnormal clinical symptom, and any toxic change was not observed in change of body weight, gross finding, and the like. From the above results, $LD_{50}$ (Lethal dose for 50% of the animal test population) of the *Piper Longum* L. water extract was above 2 g/kg. Therefore, it is concluded that *Piper Longum* L. water extract was a safe material.

1.2 1 Week-Repeated Oral Dosing Toxicity Study

For purposes of dose setting basis in long term repeated-dose toxicity study, 1 week-repeated oral dose toxicity study was performed using specific pathogen-free (SPF) female ICR mouse (ORIENT, Korea). The animals were divided into 5 rats per group. The 30% by volume aqueous ethanol solution extract of the *Piper Longum* L. prepared in Preparation Example 1.2 was orally administered once a day for 7 days at dose levels of 1000, 500 and 250 mg/kg. After administration of experimental material, mortality, clinical symptom and change of body weight were observed, and gross finding of organs in abdominal and thoracic cavity was performed after necropsy.

There were no dead animals in all dosing groups. Although a tendency to slight decreases in body weight and movement were observed up to 2 days after starting administration in 1000 mg/kg dosing group, these changes were then recovered to normal after 2 days. From the above results, abnormal clinical symptom, change of body weight and toxic change in gross finding were not observed. From the above results, the 30% by volume aqueous solution of ethanol extract of the *Piper Longum* L. was identified as a safe material not showing toxicity, even if it was repeatedly administered to the mouse up to 1 g/kg for 1 week.

1.3 4 Weeks-Repeated Oral Dosing Toxicity Study

To identify toxicity on long term dose, 4 weeks-repeated oral dosing toxicity study was performed using specific pathogen-free (SPF) ICR mouse. The animals were divided into 5 rats per group. Water extract of the *Piper Longum* L. prepared in Preparation Example 1.1 was orally administered once a day for 28 days at dose levels of 2000, 1000, 500, 250 and 125 mg/kg. After administration of experimental material, mortality, clinical symptom and change of body weight were observed, and gross finding of organs in abdominal and thoracic cavity was performed after necropsy.

There were no dead animals and abnormal clinical symptom, and any toxic change in change of body weight and gross finding was not observed. From the above results, the water extract of *Piper Longum* L. was identified as a safe material not showing toxicity, even if it was repeatedly administrated to the mouse up to 2 g/kg for 4 weeks.

1.3 Repeated-Dose Toxicity Experiment for 4 Weeks

To identify toxicity on long term dose, repeated-oral dose toxicity experiment for 4 weeks was performed using specific pathogen-free (SPF) ICR mouse. The water extract of *Piper Longum* L. prepared in Preparation Example 1.1 was oral administrated to 5 experimental animals per group in a dose of 2000, 1000, 500, 250, 125 mg/kg at once a day for 28 days. After administration of experimental material, whether or not for the animals to have been died, clinical symptoms, and change in body weight were observed, and then abnormality of organs in abdominal cavity and thoracic cavity was observed with the naked eye after autopsy.

As a result, there was no animal with specifically noted clinical symptoms and being died in all the animals that the experimental material was administrated, and moreover change in toxicity was not observed from change in body weight and autopsy manifestation, and the like. From the above results, the water extract of *Piper Longum* L. was identified as a safe material not to show toxicity, even if it was repeatedly administrated to the mouse up to 2 g/kg for 4 weeks.

Preparation Example 2: Preparation of Extracts of *Piper Longum* L.

Using water and an organic solvent, such as ethanol, methanol, ethyl acetate, isopropanol, dichloromethane, chloroform and n-hexane as an extraction solvent, extracts of *Piper Longum* L. were prepared, respectively.

Preparation Example 2.1: Preparation of Water Extract of *Piper Longum* L.

Using 100 mL of purified water, each 5 g of the fruits of *Piper Longum* L. dried in shade was extracted in a constant temperature water bath (HYNDAE Science, B-90) at 80-90° C. for 3 hours under reflux. The resulting extract was filtered with a filter paper under reduced pressure, and then the resulting filtrate was evaporative concentrated with a vacuum rotary evaporator (EYELA, N-1100) under a condition of 50-60° C. and dried with a vacuum dryer (JEIO Tech, OV-12) for at least 12 hours to yield 0.76 g of water extract of *Piper Longum* L., which was represented in Table 1 below.

Preparation Example 2.2: Preparation of Organic Solvent Extracts of *Piper Longum* L.

Extracts were prepared by the same method as the above Preparation Example 2.1 except that ethanol, 95% by volume of aqueous solution of ethanol, methanol, and ethyl acetate were used as an extraction solvent instead of water, respectively. Then, when the solvent as an extraction solvent was changed into dichloromethane, chloroform, and hexane, respectively, extracts were prepared by the same method as the above Preparation Example 2.1 except that they were extracted in a constant temperature water bath (HYNDAE Science, B-90) at 60-70° C. 0.21 g to 0.81 g of extracts were obtained, which were specifically represented in Table 1.

TABLE 1

| Crude drug weight | Extraction solvent | Yield Amount (g) | Yield (%) |
|---|---|---|---|
| 5 g | Water | 0.76 | 15.28 |
| 5 g | Ethanol | 0.54 | 10.96 |
| 5 g | 95% aqueous solution of ethanol | 0.61 | 12.2 |
| 5 g | Methanol | 0.56 | 11.12 |
| 5 g | Ethyl Acetate | 0.81 | 16.12 |
| 5 g | Isopropanol | 0.47 | 9.4 |
| 5 g | Dichloromethane | 0.44 | 8.84 |
| 5 g | Chloroform | 0.24 | 4.82 |
| 5 g | n-Hexane | 0.21 | 4.16 |

Preparation Example 2.3: Preparation of Aqueous Solution of Ethanol Extracts of *Piper Longum* L. According to Concentrations Extracts were prepared by the same method as the above Preparation Example 2.1 except that 30% by volume, 50% by volume, 70% by volume, and 95% by volume of aqueous solution of ethanols were used as an extraction solvent. 0.61 g to 0.86 g of extracts were obtained, which were specifically represented in Table 2.

TABLE 2

| crude drug weight | Extraction solvent | Yield Amount (g) | Yield (%) |
|---|---|---|---|
| 5 g | 95% aqueous solution of ethanol | 0.61 | 12.2 |
| 5 g | 70% aqueous solution of ethanol | 0.86 | 17.2 |
| 5 g | 50% aqueous solution of ethanol | 0.83 | 16.52 |
| 5 g | 30% aqueous solution of ethanol | 0.71 | 14.12 |

Preparation Example 2.4: Preparation of Organic Solvent Fractions of 95% by Volume of Aqueous Solution of Ethanol Extracts of *Piper Longum* L.

Using about 10 L of 95% by volume of aqueous solution of ethanol, 1 kg of the *Piper Longum* L. fruits dried in shade was extracted twice in a constant temperature water bath (JISICO, J-BAL) for 3.5 hours under reflux. The resulting extract was filtered with a filter paper under reduced pressure, and then the resulting filtrate was evaporative concentrated with a vacuum rotary evaporator (EYELA, N-1100) under a condition of 50-60° C. and dried with a vacuum dryer (JE10 Tech, OV-12) for at least 12 hours to yield 82.99 g of 95% by volume of aqueous solution of ethanol extract of the *Piper Longum* L. The 95% by volume of aqueous solution of ethanol extract of the *Piper Longum* L. was suspended by adding 1.5 L of distilled water to a fraction funnel, shaken by adding 1.2 to 1.5 L of an organic solvent to confirm separating layers of the organic solvent, and then a procedure of concentration under reduced pressure was carried out by taking the corresponding organic solvent.

Using dichloromethane, ethyl acetate, water-saturated n-butanol in order, the process was carried out to prepare the organic solvent fractions (56.13 g to 2.2 g), and the fraction (about 10 g) of the aqueous layer excluding organic solvent layers, which were represented in Table 3 below.

TABLE 3

| Extract Weight | Fraction Solvent | Yield Amount (g) | Yield (%) |
|---|---|---|---|
| 82.99 g | Dichloromethane | 56.13 | 67.63 |
| | Ethyl acetate | 3.01 | 3.63 |
| | Saturated n-butanol | 2.20 | 2.65 |
| | Aqueous layer excluding organic solvent layers | about 10.00 | about 12.05 |

Example 2: Measurement of Effect of Inhibiting Activity of Muscarinic $M_3$ Receptor The human bladder smooth muscle Cells (hBdSMC) where the muscarinic $M_3$ receptor had been expressed were purchased from Lonza (cambrex), and used. A medium for smooth muscle cells (SmGM-2) including fetal bovine serum (5%), recombinant growth factors (human epidermal growth factor; hEGF, human fibroblast growth factor; hFGF), antibiotic (Gentamicin), and insulin, which was also purchased from Lonza (cambrex), was used as a culture fluid, and the above cells were sub-cultured in 5% $CO_2$ incubator by passage 10~13. The cultured cells seeded in a 6 well plate, and after 24 hours, were cultured in serum free DMEM medium for another 48 hours. The extracts of *Piper Longum* L. prepared in Preparation Example 2 were made into concentrations represented in Tables 4 and 5 to pre-treat the cultured cells for 2 hours, to which 25 μM of acetylcholine (Ach) causing detrusor contraction was administrated for 2 minutes to induce activity of the $M_3$ receptor. Cells that no acetylcholine and extract of *Piper Longum* L. were treated and cells that 25 μM of acetylcholine was treated alone were used as a control group. The above cells were cleaned with ice-cold PBS, dissolved in a buffer solution for lysis (100 mM NaCl, 0.75% DOC (deoxycholic acid), 0.5% SDS (sodium dodecyl sulfate), 1 mM DTT (Dithiothreitol), 20 mM Tris/HCl·pH8.0), and centrifuged, and then the supernatant was separated by SDS-PAGE (Sodium Dodecyl Sulfate Poly-Acrylamide Gel Electrophoresis). Then, using phospho-$MLC_{20}$ (p-$MLC_{20}$ antibody), activity of $MLC_{20}$ (myosin light chain), which is the most important for contraction of smooth muscle cells, was identified via western blot method (Biochem. J. (2003) 374:145), and the activated degree was quantified with a densitometer (Bio-rad, GS-700). Based on the resulting value in well of the control group that acetylcholine only was placed therein to be 0% inhibition, inhibition rates (%) of $MLC_{20}$ activity (p$MLC_{20}$) according to concentrations of drugs were calculated, and the results were represented in Tables 4 and 5 below.

TABLE 4

| Extract of *Piper Longum* L. | Dose (μg/ml) | p$MLC_{20}$ inhibition rate (%) |
|---|---|---|
| 100% Ethanol | 25 | 63.2 |
| | 50 | 74.9 |
| 95% aqueous solution of ethanol (spirit) | 25 | 43.88 |
| | 50 | 92.29 |
| Methanol | 25 | 34.8 |
| | 50 | 65.2 |

TABLE 4-continued

| Extract of *Piper Longum* L. | Dose (μg/ml) | p$MLC_{20}$ inhibition rate (%) |
|---|---|---|
| Ethyl Acetate | 25 | 83.9 |
| | 50 | 87.7 |
| Isopropanol | 25 | 73.6 |
| | 50 | 46.3 |
| n-Hexane | 25 | 46.6 |
| | 50 | 36.3 |
| Chloroform | 25 | 37.9 |
| | 50 | 92.6 |
| Dichloromethane | 25 | −15.3 |
| | 50 | 68.4 |
| Water | 500 | 54.1 |
| | 1000 | 85.6 |

TABLE 5

| Extract of *Piper Longum* L. | | Dose (μg/ml) | p$MLC_{20}$ inhibition rate (%) |
|---|---|---|---|
| 95% aqueous ethanol (spirit) solution | | 50 | 99.95 |
| | | 100 | 98.55 |
| 70% aqueous solution of ethanol | | 50 | 92.21 |
| | | 100 | 99.53 |
| 50% aqueous solution of ethanol | | 50 | 50.12 |
| | | 100 | 71.37 |
| 30% aqueous solution of ethanol | | 100 | 45.7 |
| | | 200 | 74 |
| 95% aqueous solution of ethanol | Dichloromethane fraction | 25 | 97.9 |
| | | 50 | 81.5 |
| | Ethyl acetate fraction | 25 | 46.3 |
| | | 50 | 70.5 |
| | Saturated n-butanol fraction | 25 | 3.7 |
| | | 50 | 36.2 |
| | Water fraction excluding organic solvent layers | 25 | 12.4 |
| | | 50 | 23.8 |

As a result of searching inhibition rates of activity by extracts of *Piper Longum* L. following inducing $MLC_{20}$ activity involved in involuntary detrusor contraction by treating human bladder smooth muscle cells with acetylcholine being a neutrotransmitter, it could be known that the extracts *Piper Longum* L. extracted from various solvents reveal inhibition activity, as shown in Table 4 above. Based on results of extracts of *Piper Longum* L. from these solvents, extracts according to ethanol contents and fractions of 95% ethanol extract were prepared via the method described in Preparation Example 2 to measure $MLC_{20}$ activity by the same method above. As a result, all the extracts extracted from aqueous solution of ethanol containing at least 30% by volume of ethanol showed inhibition rates of at least 45~50% in treatment groups of 100 μg/ml as in Table 5, and dichloromethane and ethyl acetate fractions of 95% ethanol extract also showed high inhibition of $MLC_{20}$ activity. Through the above results, it is supposed that extracts of *Piper Longum* L. and fractions of ethanol extract according to the present invention inhibit detrusor over activity (contraction) induced by acetylcholine, and the like, which is transmitted via $M_3$ receptor in urine storage phase, to have effects of improving voiding dysfunction.

Preparation Example 3: Preparation of 95% by Volume of Aqueous Solution of Ethanol Extract of *Piper Longum* L.

7 L of 95% by volume of aqueous solution of ethanol was added to 700 g of the dried *Piper Longum* L. fruits after drying in shade to be extracted at 95° C. for 3.5 hours under reflux. The resulting extract was filtered, and then concentrated under reduced pressure in a condition of 50-60° C. with a vacuum rotary evaporator to yield 52.7±0.1 g of soft extract of 95% by volume of aqueous solution of ethanol extract of the *Piper Longum* L., which was used in the following experiment.

Example 3: Measurement of Effect of Inhibiting Muscarinic $M_2$ Receptor Activity It is known that when muscarinic $M_2$ receptor, which is one of GPCR (G protein-coupled receptors), is coupled with acetylcholine being an agonist it inhibits activity of adenylyl cyclase enzyme to decrease a concentration of cAMP in cells, in which if the amount of cAMP increases, detrusor is relaxed, or otherwise if the amount of cAMP decreases, detrusor is contracted. Therefore, in confirming improvement of voiding dysfunction, it is important to identify an effect of being capable of increasing or decreasing the amount of cAMP. Accordingly, it was identified whether or not the extract of *Piper Longum* L. has activity of inhibiting muscarinic receptor that may inhibit decrease of a concentration of cAMP by acetylcholine, by pre-treating 95% by volume of aqueous solution of ethanol extract of *Piper Longum* L., treating it with acetylcholine which may serve as an activator of muscarinic $M_2$ receptor to induce decrease of a concentration of cAMP, and treating it with Forskolin that may raise a concentration of cAMP in cells. More specifically, the procedure is as follows.

The human bladder smooth muscle Cells (hBdSMC) where the muscarinic $M_2$ receptor had been expressed were purchased from Lonza (cambrex), and used. A medium for smooth muscle cells (SmGM-2) including fetal bovine serum (5%), recombinant growth factors (hEGF, hFGF), antibiotic (Gentamicin), and insulin, which was also purchased from Lonza (cambrex), was used as a culture fluid, and the above cells were sub-cultured in 5% $CO_2$ incubator by passage 10~13. The cultured human bladder smooth muscle cells (hBdSMC) were grown to confluence in a 24 well plate, and then washed with PBS, pre-treated with 0.5 mM 3-isobutyl-l-methylxanthine (IBMX) in serum free DMEM medium for 30 minutes, and treated with oxybutynin being a control drug or ethanol extracts of *Piper Longum* L. prepared in Preparation Example 3 at each concentrations for 30 minutes. Then, after administrating 10 μM of acetylcholine (ACh) thereto for 5 minutes, they were cultured with 10 μM of Forskolin for 15 minutes, and the reaction was completed by adding 0.1M HCl. The amount of cAMP in cells was evaluated by measuring absorbance (408 nm) with an ELISA kit from the supernatant taken after centrifuging cells dissolved in 0.1M HCl.

The results were represented in Table 6 below.

TABLE 6

|  | μg/ml | cAMP (pmol/ml) | % of forskolin |
|---|---|---|---|
| Control |  | ND | — |
| Forskolin (F) 10 μM |  | 30.86 | 100 |
| F + ACh 10 μM |  | 3.56 | 11.54 |
| F + ACh + oxybutynin 10 μM |  | 28.21 | 91.39 |
| F + ACh + *Piper Longum* L. (95% aqueous solution of ethanol) | 20 | 12.25 | 39.68 |
|  | 75 | 16.5 | 53.47 |
|  | 150 | 26.19 | 84.82 |

As shown in Table 6 above, the group treated with acetylcholine alone reduced dramatic increase of cAMP in cells induced by directly activating adenylyl cyclase enzyme with Forskolin to a level of about 11%, whereas the experimental group treated with extracts of *Piper Longum* L. increased a concentration of cAMP depending on treatment concentrations of extracts of *Piper Longum* L. That is, it could be demonstrated that the extracts of *Piper Longum* L. may increase a concentration of cAMP in cells by inhibiting muscarinic $M_2$ receptor to relieve inhibition of accumulating cAMP in cells. Specifically, the experimental group treated with 150 μg/ml of the extract of *Piper Longum* L. revealed the outstanding effect to recover a concentration of cAMP level to 84.82% of the group treated with Foskolin alone. It can be seen from such a result that the extracts of *Piper Longum* L. may be used as a material which can serve to relax detrusor effectively by increasing the cAMP amounts.

Example 4: Measurement of Effect of Activating $β_3$-Adrenergic Receptor

Since $β_3$-adrenergic receptor was known to be involved in relaxation of detrusor via cAMP signaling pathway, the effect of improving voiding abnormal symptoms on the extracts of *Piper Longum* L. was confirmed by measuring cAMP amounts in cells being its activation parameter. SK-N-MCs (neuroblastoma cells) where $β_3$ and $β_1$-adrenergic receptors had been overexpressed were dispensed into 24 well plate at $5 \times 10^5$ cells/well, rinsed with PBS after 24 hours, and then transferred into a serum free medium, and pre-treated with 0.5 mM of 3-isobutyl-l-methylxanthine (IBMX) and 5 μM of CGP-20712A being an antagonist of $β_1$-adrenergic receptor to exclude $β_1$-adrenergic receptor effect for 30 minutes. This pre-treatment was carried out in order to exclude an effect by $β_1$-adrenergic receptor and identify change of cAMP amounts by $β_3$-adrenergic receptor effect. The extract of *Piper Longum* L. from Preparation Example 2 was made to concentrations represented in the following table, administrated to the treated cells, and reacted in an incubator for 30 minutes, and then the cells were dissolved by adding 0.1M HCl. The amounts of cAMP in cells were measured with an ELISA kit, with comparing the extracts treatment group with the untreated control group with the extracts, and the results were represented in Tables 7 and 8 below.

TABLE 7

| Extracts of *Piper Longum* L. | μg/ml | Fold of Con |
|---|---|---|
| Control | — | 1 |
| 95% aqueous solution of ethanol | 50 | 2.646 |
|  | 100 | 3.338 |
|  | 200 | 3.829 |
| Dichloromethane | 50 | 2.81 |
|  | 100 | 3.00 |
|  | 200 | 3.36 |
| 100% Ethanol | 50 | 2.41 |
|  | 100 | 2.04 |
| 100% Methanol | 50 | 2.22 |
|  | 100 | 2.57 |
|  | 200 | 3.22 |
| Water | 200 | 2.26 |
|  | 500 | 2.11 |
|  | 1000 | 2.81 |

TABLE 8

| Extracts of *Piper Longum* L. | | μg/ml | Fold of Con |
|---|---|---|---|
| Control | | — | 1.00 |
| 70% Aqueous solution of ethanol | | 50 | 1.69 |
| | | 100 | 2.20 |
| 50% Aqueous solution of ethanol | | 50 | 1.62 |
| | | 100 | 2.16 |
| 30% Aqueous solution of ethanol | | 50 | 2.47 |
| | | 100 | 2.09 |
| 95% Aqueous solution of ethanol | Dichloromethane fraction | 50 | 2.62 |
| | | 100 | 2.54 |
| | Ethyl acetate fraction | 50 | 1.25 |
| | | 100 | 1.85 |
| | Saturated n-butanol fraction | 50 | 1.28 |
| | | 100 | 1.91 |
| | Water fraction excluding organic solvent layers | 50 | 1.06 |
| | | 100 | 1.08 |

As shown in Table 7 above, the ethanol extract of *Piper Longum* L. evidently increased the amount of cAMP in cells depending on concentrations, as compared with the untreated control group with the extract of *Piper Longum* L., and in the treated group with extract of *Piper Longum* L. at 100 μg/ml or more, the outstanding effect on increase of cAMP by a factor of 3 or more could be identified. In addition, it was shown that the water extract of *Piper Longum* L. as well as the dichloromethane and methanol extracts of *Piper Longum* L. increased the amount of cAMP. In accordance with the results of 95% ethanol extracts in Table 7 above, the cells were treated with the extracts according to ethanol contents and the fractions of 95% ethanol extract by the same method above to measure the amounts of cAMP in cells, which were compared with the control group. As a result, the effect of increasing cAMP by a factor of about 2 or more could be identified in group of 100 μg/ml from all the extracts extracted from aqueous solution containing at least 30% by volume of ethanol relative to the control group, as in Table 8, and the effect of increasing cAMP was also identified even in dichloromethane fraction of 95% ethanol extract. Therefore, it was shown that the aqueous solution of ethanol extracts of *Piper Longum* L. extracted with hydrous ethanol at various concentrations and various organic solvent fractions of aqueous solution of ethanol extracts may induce relaxation of detrusor.

According to the results above, the extracts of *Piper Longum* L. were identified to be materials such that they may inhibit activity of $MLC_{20}$ induced by acetylcholine, effectively relieve inhibition of accumulating cAMP in cells via muscarinic $M_2$ receptor and increase the amount of cAMP in cells, which is an parameter of activity of $\beta_3$-adrenergic receptor involved in relaxation of detrusor. Therefore, the extracts of *Piper Longum* L. can be supposed to have a treatment or improvement effect on voiding abnormal symptoms, since they may not only serve as an antagonist of muscarinic $M_3/M_2$ receptors by inhibiting these receptors and signaling systems related thereto, but also inhibit contraction of detrusor and induce relaxation of detrusor via combined actions of agonistic actions of $\beta_3$-adrenergic receptor.

Preparation Example 4: Preparation of Extracts of *Piper Longum* L.

Preparation Example 4.1: Preparation of 95% Aqueous Solution of Ethanol Extract of *Piper Longum* L.

To further identify an effect of improving voiding dysfunction in animal models by extracts of *Piper Longum* L., 95% aqueous solution of ethanol extract and water extract of *Piper Longum* L. were prepared. 1.0 L of 95% by volume of aqueous solution of ethanol was added to 200 g of the fruits of *Piper Longum* L. and was extracted twice at 95° C. for 3.5 hours under reflux. The resulting extract was filtered, and then concentrated to dryness to prepare 95% aqueous solution of ethanol extract.

Preparation Example 4.2: Preparation of Water Extract of *Piper Longum* L.

The water extract of *Piper Longum* L. was prepared using the same method as the preparation of 95% by volume of ethanol extract in the above Preparation Example 4.1 except that the extraction solvent was changed to water.

Example 5: Effect of Controlling Micturition Pressure and Micturition Interval in CYP-Induced Cystitis Model Pretreated with *Piper Longum* L. Extracts for 7 Days The effect of *Piper Longum* L. extracts on micturition pressure and bladder capacity was identified using CYP-induced cystitis rat model.

Cycolphosphamide (referred to CYP below)-induced rat model as cystitis animal model has advantages that the inflammation occurred only in the bladder within a few hours after dosing and surgical procedure or tracheal intubation is not required. In addition, pain types and voiding symptoms are similar to human because CYP also causes cystitis in human (The Effect of Botulinum Toxin and Resiniferatoxn on the Detrusor Overactivity Induced by Cyclophophamide in Rat Bladder, Korean Journal of Urology: Vol. 47 No. 1, 2006). Therefore, CYP induces bladder over activity in bladders of animal and human by chemical inflammation to show detrusor over activity in urodynamic study together with irritable voiding symptoms so that CYP-induced cystitis rat model is considered as an animal model for overactive bladder (Journal of physiology and pharmacology 2009, 60, 4, 85-91. Urodynamic effects of the bladder c-fiber afferent activity modulation in chronic model of overactive bladder in rats).

5.1. Experimental Animal 20 specific pathogen-free (SPF) female SD rats (8-week old upon receipt) were purchased from ORIENT (Korea) and used. Day and night were controlled by a 12 hour cycle, and they were allowed to access to food and water freely.

5.2. Effect of *Piper Longum* L. Extracts on Improving Urodyanmic Parameters

To measure bladder pressure and micturition interval, which are parameters for identifying improvement of voiding dysfunction, cyclophosphamide (150 mg/kg) was once intraperitoneally administered to rats excluding a normal control group to induce irritable bladder symptoms at 3 days before cystometry. From 7 Days before cystometry, a solvent (DMSO/10% Cremophor EL=1:9, vol/vol) had been administered to a solvent control group, and 95% by volume of aqueous ethanol solution extract of *Piper Longum*

L. fruits prepared in Preparation Example 4.1 had been administrated to an experimental group at 200 mg/kg. For cystometry and injection of a physiological saline solution, after a rat was anesthetized on the day of measuring urodynamic parameters, a cuffed polyethylene catheter (PE-50, Becton Dickinson, Parsippany, USA) was fixed on its bladder dome with purse-string suture via the center incision of its lower abdomen. After carrying out insertion of a bladder vessel and a vessel for measuring an abdominal pressure, the bladder vessel of the rat was coupled to a microinjection pump (KDS100 Single Syringe Infusion Pump; KD Scientifics) and a pressure transducer (GRASS MODEL 7 POLYGRAPH; GRASS instrument Co. U.S.A) with a 3-way cock. Then, 30 minutes after insertion, urodynamic parameters such as an intravesical pressure were measured, with injecting a physiological saline solution at a speed of 0.04 ml/min for 2 hours using an intravesical infusion pump. Analysis of intravesical pressure data acquisition was observed with Chart 4 PowerLab (ADinstument, USA), and 4~5 continuous micturition contraction peaks prior to and after administration of drug in the measured voiding cycles were each selected to be averaged.

The measured values of urodynamic study in CYP animal models and their definitions are as follows.

A basal pressure (BP), which is an parameter of intravesical pressure in 5 repeated voiding cycles, is the lowest pressure in cystometry, a threshold pressure (TP) is a pressure immediately before micturition contraction, and a micturition pressure (MP) means the maximum bladder pressure represented on voiding. A micturition interval (MI) was determined by calculating a time interval between consecutive micturition pressures. The voiding cycles were measured for 120 minutes, and the average values of each parameter were calculated by selecting the most representative 5 continuous cycles among the measured voiding cycles.

The results were represented in Table 9 and FIG. 1 below.

threshold pressure (TP) which is a parameter of measuring bladder pressure related to a storage function of bladder.

Example 6: Effect of *Piper Longum* L. Extracts on Micturition Pressure, Bladder Capacity and Micturition Interval in CYP-Induced Cystitis Model after Dosing the Extracts of *Piper Longum* L. for 3 Days 6.1. Experimental Animal 65 of specific pathogen-free (SPF) SD female rats were purchased from ORIENT (Korea) and used. Day and night were controlled by a 12 hour cycle, and they were allowed to access to food and water freely.

6.2. Effect of *Piper Longum* L. Extracts on Improving Urodynamic Parameters

To measure bladder pressure, bladder capacity and voiding volume, which are parameters for identifying improvement of voiding dysfunction, cyclophosphamide (150 mg/kg) was once intraperitoneally administered to rats excluding a normal control group to induce irritable bladder symptoms at 3 days before cystometry. From 3 Days before cystometry, a solvent (DMSO/10% Cremophor EL=1:9, vol/vol) had been administrated to a solvent control group, and 95% by volume of aqueous ethanol solution extract of *Piper Longum* L. fruits prepared in Preparation Example 4.1 had been administrated to an experimental group at 200 mg/kg. In addition, oxybutynin as a positive control group was injected via a caudal vein at 0.3 mg/kg on the day of experiment.

For cystometry and injection of a physiological saline solution, instruments for cystometry and insertion of a bladder vessel were the same as in the above Example 5.2, and voiding volume and residual volume were recorded by sampling urine in a 1.5 ml tube and measuring its weight.

The measured values of urodynamic study in CYP animal models and their definitions are as follows.

The basal pressure (BP), threshold pressure (TP), micturition pressure (MP) and micturition interval (MI) which are defined as in the above Example 5.2. In addition, a voiding volume being an parameter of volume parameter was defined by sampling urine in a 1.5 ml tube on the last voiding

TABLE 9

| Urodynamic parameter related to pressures and micturition intervals | | | | |
|---|---|---|---|---|
| Group | BP (cm H$_2$O) | MP (cm H$_2$O) | TP (cm H$_2$O) | MI (sec.) |
| Normal Control Group | 10.5 ± 3.06 | 29.14 ± 4.13 | 18.21 ± 3.14 | 258.04 ± 44.10 |
| Solvent Control Group | 17.9 ± 5.35* | 29.05 ± 2.29 | 24.28 ± 2.50** | 124.48 ± 50.60* |
| Group treated with 95% by volume of aqueous solution of ethanol extract of *Piper Longum* L. | 10.46 ± 5.66 | 29.83 ± 7.30 | 17.05 ± 4.77# | 195.90 ± 92.91 |

Result: Mean ± Standard Deviation
*,**Significance for normal control group, (*p < 0.05, **p < 0.01 vs normal control group)
##Significance for OAB (Overactive bladder) control group (solvent control group), (#p < 0.05, ##p < 0.01 vs solvent control group)
One-way ANOVA or Mann-Whitney U Test As can be seen from the above Table 9 and FIG. 1, it was demonstrated that the ethanol extract of *Piper Longum* L. outstandingly increased the micturition interval to 195.90±92.91, compared with the solvent control group of overactive bladder syndromes untreated with extract of *Piper Longum* L., and maintained evenly all of BP, IMP, MP, and TP which are various bladder pressure indices to the levels of the normal control group, and in particular, it was identified to show the effect of significantly improving the during urodynamic measurements and measuring its weight. After completing micturition, a residual volume was defined by placing the catheter inserted into bladder at the lower portion than the rat and measuring the weight of the obtained physiological saline. A bladder capacity (BC) was calculated by combining the measured residual volume (RV) and voiding volume (VV) of the rat.

The voiding cycles were measured for 120 minutes, and the average values of each parameter were calculated by selecting the most representative 5 continuous cycles among the measured voiding cycles.

The results were represented in Table 10 and FIG. 2.

TABLE 10

Urodynamic parameters related to volume and blader weight

| Group | BP (cm H$_2$O) | MP (cm H$_2$O) | TP (cm H$_2$O) | VV (ml) | RV (ml) | BC (ml) | MI (sec.) |
|---|---|---|---|---|---|---|---|
| Normal Control Group | 6.1 ± 3.4 | 25.8 ± 4.9 | 12.5 ± 3.3 | 0.23 ± 0.08 | 0.32 ± 0.27 | 0.55 ± 0.26 | 228.81 ± 50.50 |
| Solvent Control Group | 22.1 ± 9.6** | 64.6 ± 18.2** | 32.5 ± 11.4** | 0.09 ± 0.08* | 0.23 ± 0.05 | 0.27 ± 0.10** | 103.67 ± 18.81** |
| Oxybutynin 0.3 mg/kg | 9.7 ± 3.1## | 29.2 ± 7.9# | 17.6 ± 4.3## | 0.16 ± 0.08 | 0.30 ± 0.13 | 0.46 ± 0.14# | 221.54 ± 75.20## |
| 95% by volume of aqueous ethanol solution extract of *Piper Longum* L. | 9.7 ± 4.3## | 29.5 ± 14.6## | 17.7 ± 6.0## | 0.16 ± 0.05 | 0.28 ± 0.12 | 0.43 ± 0.13 | 154.74 ± 41.18*,# |

Result: Mean ± Standard Deviation
*, **Significance for normal control group, (*p < 0.05, **p < 0.01 vs normal control group)
, ##OAB (Overactive bladder) Significance for control group (solvent control group), (#p < 0.05, ##p < 0.01 vs solvent control group)
One-way ANOVA or Mann-Whitney U Test As shown in the above Table 10 and FIG. 2, the ethanol extract of *Piper Longum* L. revealed the effect of significantly improving micturition interval (MI), which is a parameter related to frequent urination as represented in overactive bladder of voiding dysfunction state, over the solvent control group induced by overactive bladder symptoms. In addition, it also revealed the effect of improving overactive bladder symptoms on basal pressure (BP), micturition pressure (MP), and threshold pressure (TP) on non-voiding which are parameters for measuring bladder pressure related to storage function of bladder. It was identified that voiding volume (VV) could be improved to a level similar to a group treated with oxybutynin as a positive control group.

6.3. Effects of Ethanol and Water Extracts of *Piper Longum* L. on Improving Urodynamic Parameters It was identified whether water extract of the *Piper Longum* L. could also improve the urodynamic parameters. More specifically, the effect of improving urodynamic parameters was evaluated using CYP animal models by the same method as the above Example 6.2 except that they were treated with water extract of *Piper Longum* L. in Preparation Example 4.2 as an additional experimental group, in addition to 95% by volume of ethanol extract of *Piper Longum* L. in Preparation Example 4.1, and compared by measuring the voiding volume and the micturition interval (MI) which are representative parameters evaluating voiding dysfunction related to overactive bladder syndromes.

The results were represented in Table 11 and FIG. 3 below.

TABLE 11

| Group | VV (ml) | MI (Sec.) |
|---|---|---|
| Normal Control Group | 0.14 ± 0.07 | 212.5 ± 85.96 |
| Solvent Control Group | 0.09 ± 0.05 | 88.41 ± 22.59** |
| Group treated with Oxybutynin 0.3 mg/kg | 0.24 ± 0.15# | 248.50 ± 144.43## |
| Group treated with 95% by volume of aqueous solution of ethanol extract of *Piper Longum* L. | 0.18 ± 0.05# | 194.14 ± 52.10## |
| Group treated with water extract of *Piper Longum* L. | 0.19 ± 0.05# | 207.06 ± 82.75## |

Mean ± Standard Deviation
*,**Significance for normal control group (p < 0.05, 0.01)
,##Significance for solvent control group (p < 0.05, 0.01)

As can be seen from the above Table 11 and FIG. 3, both ethanol and water extracts of *Piper Longum* L. increased the voiding volume (VV) to a very significant extent relative to solvent control groups of overactive bladder, and also outstandingly increased the micturition interval (MI) by a factor of about 2 or more relative to the solvent control groups. According to the results above, since both water and ethanol extracts of *Piper Longum* L. could improve micturition interval decrease and voiding volume decrease concomitant with voiding dysfunction, they were identified to be materials having the excellent effect being capable of preventing or treating various voiding dysfunctions such as overactive bladder syndromes accompanying frequent urine, urgency urine, and the like in a similar level of the commercially available oxybutynin.

Preparation Example 5: Preparation of the Extracts of *Piper Longum* L.

Preparation Example 5.1: Preparation of the Water Extract of *Piper Longum* L.

6.0 L of water was added to 1 Kg of the fruits of *Piper Longum* L. dried in shade to be extracted twice in a constant temperature water bath (HYNDAE Science, B-90) at 80-90° C. for 3.5 hours under reflux. The resulting extract was filtered with a filter paper under reduced pressure, and then the resulting filtrate was evaporative concentrated with a vacuum rotary evaporator (EYELA, N-1100) under a condition of 50-60° C. and dried with a vacuum dryer (JEIO Tech, OV-12) for at least 12 hours to yield the water extract of *Piper Longum* L.

Preparation Example 5.2: Preparation of 30% by Volume of Aqueous Solution of Ethanol Extract of *Piper Longum* L.

6.0 L of 30% by volume of aqueous solution of ethanol was added to 1 Kg of the fruits of *Piper Longum* L. dried in shade to be extracted twice in a constant temperature water bath (HYNDAE Science, B-90) at 80-90° C. for 3.5 hours under reflux. The resulting extract was filtered with a filter paper under reduced pressure, and then the resulting filtrate was evaporative concentrated with a vacuum rotary evaporator (EYELA, N-1100) under a condition of 50-60° C. and dried with a vacuum dryer (JEIO Tech, OV-12) for at least 12 hours to yield the 95% by volume of aqueous solution of ethanol extract of *Piper Longum* L.

Preparation Example 5.3: Preparation of 95% by Volume of Aqueous Solution of Ethanol Extract of *Piper Longum* L.

7.0 L of 95% by volume of aqueous solution of ethanol was added to 700 g of the fruits of *Piper Longum* L. dried in shade to be extracted twice in a constant temperature water bath (HYNDAE Science, B-90) at 80-90° C. for 3.5 hours under reflux. The resulting extract was filtered with a filter paper under reduced pressure, and then the resulting filtrate was evaporative concentrated with a vacuum rotary evaporator (EYELA, N-1100) under a condition of 50-60° C. and dried with a vacuum dryer (JEIO Tech, OV-12) for at least 12 hours to yield the 95% by volume of aqueous solution of ethanol extract of *Piper Longum* L.

The detail was represented in Table 12 below.

TABLE 12

| Crude Drug Weight | Extraction solvent | Yield Amount (g) | Yield (%) |
|---|---|---|---|
| 1 Kg | Purified water | 63.53 | 6.35 |
| 1 Kg | 30% Aqueous solution of ethanol | 70.59 | 7.06 |
| 700 g | 95% Aqueous Ethanol Solution | 52.70 | 7.53 |

Example 7: Effect of Extracts of *Piper Longum* L. Via SHR Non-Anesthetized Evaluation Model for Micturition Frequency Since the voiding dysfunction is diagnosed based on symptoms experienced by a patient, besides control of a bladder and nervous systems, a psychological factor plays an important role. Therefore, to evaluate voiding dysfunction, it is important to objectively observe voiding parameters in conscious animals. In view of such needs, research on human overactive bladder is increasing continuously using spontaneously hypertensive rat (hereinafter, referred to SHR) models. Although the spontaneously hypertensive rats were originally developed as an animal model for human hypertension, they have been recently used as an overactive bladder model, showed detrusor over activity in urodynamic study together with frequent urination, and thus considered as an objectively approved animal model for human overactive bladder (Jin L H et al. substantial detrusor over activity in conscious spontaneously hypertensive rats with hyperactive behavior. Scand J Urol Nephrol 2009; 43: 3-7). In experiments using spontaneously hypertensive rats most similar to human overactive bladder syndromes, a model to evaluate increase of micturition intervals after dosing of drug is an advanced model to evaluate a degree of improvement by various mechanisms rather than the effect by any one of mechanisms. Therefore, the effect of improving and treating overactive bladder syndromes by extracts of *Piper Longum* L. according to the present invention was identified from SHR models.

7.1 Experimental Animals

12 Week-old male SHRs were purchased from SLC (Japan) and used. Day and night were controlled by a 12 hour cycle, and they were allowed to access to food and water freely. After administrating solvents and drugs in Preparation Example 5 to 18 week-old SHRs, an experiment for measuring micturition frequencies was carried out.

7.2 Effect of Extracts of *Piper Longum* L. on Decreasing Micturition Frequencies On the first day of the experiment on the same SHR, a solvent was administrated thereto, and on the second day, experimental drugs in Preparation Example 5.2 (water and 30% by volume of aqueous ethanol solution extracts of *Piper Longum* L.) were administrated at 300 mg/kg. The administration volumes for two days were the same at kg/10 ml. At this time, the solvent administered to a group of administrating *Piper Longum* L. water extract on the first day is distilled water (D.W), and the solvent administered to a group of administrating 30% by volume of aqueous ethanol solution of *Piper Longum* L. is DMSO/10% Cremophor EL=1:9, vol/vol.

The results of measuring the rats administered with solvents were considered as control groups for indicators of micturition frequencies, while the rats administered with experimental drugs became experimental groups.

Specifically, after administrating solvents (first day), the SHR was placed in metabolic cages, and micturition frequencies, voiding volume and single voiding volume were measured under supply of water only for 16 hours (5 PM~9 AM), using an isometric transducer (Harvard apparatus) and MP150 (BIOPAC systems model no. MP150CE), and the result was regarded as value for the control group. After administrating experimental drugs of Preparation Example 5.2 (second day) (*Piper Longum* L. water and 30% by volume of aqueous ethanol solution extract) to SHR where the solvent was administrated on the first day, the SHR was placed in metabolic cages, and micturition frequencies, voiding volume and single voiding volume were measured under supply of water only for 16 hours (5 PM~9 AM), using an isometric transducer (Harvard apparatus) and MP150 (BIOPAC systems model no. MP150CE), and the result was regarded as a value for the experimental groups. Data of micturition frequencies for 16 hours after administrating solvents (first day) and experimental drugs (second day) were compared and statically calculated (Paired Student's t-test).

The results were represented in Table 13 and FIG. 4 below.

TABLE 13

| | Group | Micturition Frequency | Voiding Volume (ml) | Single Voiding Volume (ml) |
|---|---|---|---|---|
| Water extract of *Piper Longum* L. 300 mg/kg (n = 7) | Solvent (Control Group) | 30.1 ± 6.6 | 13.98 ± 4.92 | 0.45 ± 0.11 |
| | Drug (Experimental Group) | 22.6 ± 6.2* | 11.88 ± 3.85* | 0.52 ± 0.07 |
| | Percentage Change (%) | -25.36 | -13.97 | 17.63 |

TABLE 13-continued

| Group | | Micturition Frequency | Voiding Volume (ml) | Single Voiding Volume (ml) |
|---|---|---|---|---|
| 30% by volume of aqueous ethanol solution extract of *Piper Longum* L. 300 mg/kg (n = 7) | Solvent (Control Group) | 43.1 ± 15.2 | 21.83 ± 8.22 | 0.51 ± 0.11 |
| | Drug (Experimental Group) | 20.3 ± 11.9* | 15.00 ± 8.84 | 0.75 ± 0.17* |
| | Percentage Change (%) | −50.97 | −28.23 | 48.81 | n: Number of animals used in experiment
Mean ± Standard Deviation,
*p < 0.05, (paired Student's t-test) vs. SHR Solvent Control Group As can be seen from the above Table 13 and FIG. 4, all the water extract of *Piper Longum* L. and the 30% by volume of aqueous ethanol solution extract of *Piper Longum* L. revealed significantly improving effects on micturition frequencies being a parameter related to frequent urination developed in the overactive bladder relative to the solvent control group. Specifically, the 30% by volume of aqueous solution of ethanol extract of *Piper Longum* L. also significantly increased a single voiding volume related to storage function of bladder, and thus, it was identified to have better improvement effect on overactive bladder symptoms than the water extract of *Piper Longum* L.

Example 8: Effect of *Piper Longum* L. Extracts Via Urodynamic Study in SHR Under Un-Anesthesia 8.1 Experimental Animals 12~18 Week-old male SHRs were purchased from Charles River (Japan) and used. Day and night were controlled by a 12 hour cycle, and they were allowed to access to food and water freely. All the rats had to urinate at 3-5 cycles under a condition with no administration. The micturition parameters of rats under a condition with no administration were considered as control groups for urodynamic parameters, while the rats, to which the water extract of *Piper Longum* L. fruits prepared in Preparation Example 4.2 was directly administered into gastrointestinal tracts at 300 mg/kg via catheters coupled to stomachs, became experimental groups. As a positive control group, rats administered with tolterodine at 1 mg/kg were used. The *Piper Longum* L. water extract and tolterodine-dosing groups were each set by 6 rats.

8.2. Effect of Improving Urodynamic Parameters by Extracts of *Piper Longum* L.

To measure bladder pressure, bladder capacity, voiding volume and micturition interval, which are parameters for identifying improvement of voiding dysfunction, insertion of a bladder tube and a vessel for measuring an abdominal pressure was carried out in SHR models. For cystometry and injection of a physiological saline solution, a rat was incised in center of its lower abdomen 3 days before the day of measuring urodynamic parameters, and a cuffed polyethylene catheter with a cuff (PE-50, Becton Dickinson, Parsippany, USA) was fixed on its bladder dome with purse-string suture. In addition, a polyethylene catheter (PE-10, Becton Dickinson, Parsippany, USA) with a balloon for measuring abdominal pressure was fixed on the bladder, and another polyethylene catheter (PE-10, Becton Dickinson, Parsippany, USA) was fixed following being inserted in the gastrointestinal tract. The above catheters were passed through beneath skin, and then fixed on dorsal skin, the ends of which were closed by applying heat. An un-anesthetized rat being free was placed in a metabolic cage at 3 days after inserting a bladder tube and a vessel for measuring an abdominal pressure. The tube on the back of its neck was coupled to a microinjection pump (PHD22/2000 pump; Harvard Apparatus) and a pressure transducer (Research Grade Blood Pressure Transducer; Harvard Apparatus, Holliston, USA) with a T-tube, and then intravesical pressures were measured, with injecting the physiological saline solution at room temperate at a speed of 10 ml/hour. It is to measure intravesical pressures in the rat using a principle that when a predetermined volume of physiological saline solution is filled in the bladder, it is contracted to urinate. The abdominal pressure was measured by coupling the vessel for measuring abdominal pressure to the other pressure transducer. Also, to measure a voiding volume being an indicator of volume parameter, the voiding volume was measured from a urine amount collected in a urine collector cup (fluid collector) coupled to a force displacement transducer (Research Grade Isometric Transducer; Harvard Apparatus). Analysis of data acquisition from intravesical pressures, abdominal pressures and voiding volumes was observed with MP150 data acquisition system (BIOPAC systems, Goleta, USA) and Acq Knowledge 3.8.1 software.

Beginning to measure urodynamic parameters before administration of the extracts of *Piper Longum* L. and tolterodine, records of 3 to 5 stabilized micturition cycles were obtained. Then, the *Piper Longum* L. extracts and tolterodine were orally administered after decoupling the catheter. The catheters were again coupled thereto 20 minutes after oral administration of drugs, and voiding cycles and urodynamic study were carried out by having the rat to urinate 3 to 5 times. The average values of each parameter were measured by selecting the most representative 3 continuous cycles from voiding cycles measured before and after administration of drug.

The urodynamic values in this experiment and their definitions are as follows.

In 3 repeated voiding cycles, a basal pressure (BP), which is an parameter of intravesical pressure, is the lowest pressure in cystometry, a threshold pressure (TP) is a pressure immediately before micturition contraction, and a micturition pressure (MP) means the maximum bladder pressure represented on voiding.

After completing micturition, a residual volume was deduced by placing the catheter inserted into bladder at the lower portion than the rat and measuring the weight of the obtained physiological saline.

In the SHR model, the micturition interval (MI) means a value obtained by determining a time interval between a micturition pressure in 3 voiding cycles and a micturition pressure in the next voiding cycle and deducting a time of measuring the residual urine from the time interval.

The results were represented in Table 14 and FIG. 5 below.

TABLE 14

| Group | | BP (cmH$_2$O) | TP (cmH$_2$O) | MP (cmH$_2$O) | RV (ml) | BC (ml) | VV (ml) | MI (sec.) |
|---|---|---|---|---|---|---|---|---|
| Water extract of Piper Longum L. 300 mg/kg | Before Dosing (Control Group) | 9.8 ± 2.8 | 16.8 ± 1.1 | 61.4 ± 5.9 | 0 ± 0 | 0.58 ± 0.14 | 0.58 ± 0.14 | 207.6 ± 51.0 |
| | After Dosing | 8.9 ± 1.2 | 14.8 ± 1.8 | 61.7 ± 7.4 | 0 ± 0 | 0.93 ± 0.16* | 0.93 ± 0.16* | 333.6 ± 58.8* |
| | Percentage Change (%) | — | — | — | — | 60.3% ↑ | 60.3% ↑ | 60.7% ↑ |
| Tolterodine 1 mg/kg | Before Dosing (Control Group) | 4.9 ± 1.1 | 19.0 ± 2.6 | 49.1 ± 3.0 | 0 ± 0 | 0.30 ± 0.05 | 0.30 ± 0.05 | 249.6 ± 30.6 |
| | After Dosing | 4.8 ± 1.1 | 18.1 ± 1.7 | 50.5 ± 1.7 | 0 ± 0 | 0.41 ± 0.03* | 0.41 ± 0.03* | 365.4 ± 31.8* |
| | Percentage Change (%) | — | — | — | — | 36.7% ↑ | 36.7% ↑ | 46.4% ↑ |

Mean ± Standard Deviation, *p < 0.05, (paired Student's t test) vs. SHR control group
Student's t test (*p < 0.05, **p < 0.01)

As can be seen from the above Table 14 and FIG. 5, the extracts of *Piper Longum* L. increased the micturition interval (MI) by 60.7% relative to the control group before dosing. This means that frequent urination which is the most distinct symptom of overactive bladder syndromes could be effectively improved. They also increased voiding volume (VV) and bladder capacity (BC) by 60% or more relative to the control group. From the above results, it was demonstrated that the extracts of *Piper Longum* L. according to the present invention may outstandingly improve all the voiding volume (VV), which is a volume parameter related to frequent urination as represented in overactive bladder, bladder capacity (BC) and micturition interval (MI), and reveal better effect of than the commercially available tolterodine.

Formulation Example 1: Preparation of Medicines 1.1. Preparation of Powders
Extract of *Piper Longum* L. 100 mg
Lactose 100 mg
Talc 10 mg
The above components are mixed and filled in airtight powder bags to prepare powders.

1.2. Preparation of Tablets
Extract of *Piper Longum* L. 100 mg
Corn starch 100 mg
Lactose 100 mg
Magnesium stearate 2 mg
The above components are mixed, and then compressed according to general processes for preparing tablets to prepare tablets.

1.3. Preparation of Capsules
Extract of *Piper Longum* L. 100 mg
Corn starch 100 mg
Lactose 100 mg
Magnesium stearate 2 mg
According to general processes for preparing capsules, the above components are mixed and filled in gelatin capsules to prepare capsules.

1.4. Preparation of Injections
Extract of *Piper Longum* L. 100 mg
Sterile distilled water for injection q.s.
pH regulator g.s.
According to general processes for preparing injections, it is prepared from the above components at the above amounts per ample (2 ml).

1.5. Preparation of Liquid Formulations
Extract of *Piper Longum* L. 100 mg
Sugar 20 g
Isomerized sugar 20 g
Lemon flavor q.s.
Purified water was thereto to be adjusted to 1.00 ml. According to general processes for preparing liquid formulations, the above components are mixed, and then filled in a brown vial and sterilized to prepare liquid formulations.

Formulation Example 2: Preparation of Health Functional Foods

Extract of *Piper Longum* L. 100 mg
Vitamin mixture q.s.
Vitamin A acetate 70 µg
Vitamin E 1.0 mg
Vitamin B1 0.13 mg
Vitamin B2 0.15 mg
Vitamin B6 0.5 mg
Vitamin B12 0.2 µg
Vitamin C 10 mg
Biotin 10 µg
Nicotinic acid amide 1.7 mg
Folic acid 50 µg
Calcium panthothenate 0.5 mg
Mineral mixture q.s.
Ferrous sulfate 1.75 mg
Zinc oxide 0.82 mg
Potassium dihydrogenphosphate 15 mg
Dicalcium phosphate 55 mg
Potassium citrate 90 mg
Calcium carbonate 100 mg
Magnesium chloride 24.8 mg
Although the above vitamin and mineral mixtures have been mixed from and composed of components relatively suitable to heal functional foods as the preferred example in the above composition ratio, it may be permitted to optionally vary the combination ratio, and according to general processes for preparing general health functional foods, the above components may be mixed, and then according to general methods, be used in preparing health function food compositions (for example, nutrient candy, etc.).

Formulation Example 3: Preparation of Health Functional Beverages

Extract of *Piper Longum* L. 100 mg
Citric acid 1000 mg
Oligosaccharide 100 g
Plum extract 2 g
Taurine 1 g
Adding purified water to a total of 900 ml According to general processes for preparing health functional beverages, the above components are mixed, heated with stirring at 85° C. for about 1 hour, and then the resulting solution is filtered and obtained in a sterilized 2 l container, which is sealed and sterilized, with being kept under refrigeration, and then used in preparing health functional beverage compositions according to the present invention.

Although components relatively suitable to favorite beverages have been mixed and composed as the preferred example in the above composition ratio, it may be permitted to optionally vary the combination ratio, depending on regional or racial preference such as demanding classes, demanding nations and use.

The invention claimed is:

1. A method of treating a voiding dysfunction, the method comprising administering an extract of *Piper longum* L. as an active ingredient to a subject in need thereof, thereby treating the voiding dysfunction.

2. The method of claim 1, wherein said extract of *Piper longum* L. is extracted from one or more extraction solvents selected from the group consisting of water, alcohol, glycerin, butylene glycol, propylene glycol, methyl acetate, ethyl acetate, acetone, benzene, hexane, diethyl ether, chloroform, and dichloromethane.

3. The method of claim 2, wherein said alcohol is anhydrous or hydrous lower alcohol with 1 to 4 carbon atoms.

4. The method of claim 3, wherein said anhydrous or hydrous lower alcohol is 30 to 100% by volume of methanol or ethanol.

5. The method of claim 1, wherein said extract of *Piper longum* L. increases a micturition interval.

6. The method of claim 1, wherein said extract of *Piper longum* L. decreases a micturition pressure and increases a volume of bladder.

7. The method of claim 1, wherein said extract of *Piper longum* L. induces inhibition of detrusor contraction and relaxation of detrusor.

8. The method of claim 1, wherein said extract of *Piper longum* L. extract inhibits a muscarinic $M_3$ receptor, or a muscarinic $M_2$ receptor.

9. The method of claim 1, wherein said extract of *Piper longum* L. is an agonist of a $\beta_3$-adrenegic receptor.

10. The method of claim 1, wherein said voiding dysfunction is one or more selected from the group consisting of overactive bladder syndromes, urgency incontinence, urgency urine, frequent urination, nocturia, and interstitial cystitis.

11. A method of improving a voiding dysfunction, the method comprising administering an extract of *Piper longum* L. as an active ingredient to a subject in need thereof, thereby improving the voiding dysfunction.

12. The method of claim 11, wherein said voiding dysfunction is one or more selected from the group consisting of overactive bladder syndromes, urgency incontinence, urgency urine, frequent urination, nocturia, and interstitial cystitis.

13. The method of claim 1, wherein said extract of *Piper longum* L. is a polar solvent-soluble extract, or a non-polar solvent-soluble extract.

14. The method of claim 11, wherein said extract of *Piper longum* L. is a polar solvent-soluble extract, or a non-polar solvent-soluble extract.

* * * * *